US007951997B2

(12) United States Patent
Huang et al.

(10) Patent No.: US 7,951,997 B2
(45) Date of Patent: May 31, 2011

(54) REVERSIBLE MALE STERILITY IN TRANSGENIC PLANTS BY EXPRESSION OF CYTOKININ OXIDASE

(75) Inventors: Shihshieh Huang, Stonington, CT (US); Lyle Dean Crossland, St. Louis, MO (US); Roy O. Morris, Portland, OR (US); Nordine Cheikh, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 998 days.

(21) Appl. No.: 11/735,793

(22) Filed: Apr. 16, 2007

(65) Prior Publication Data

US 2010/0242132 A1 Sep. 23, 2010

Related U.S. Application Data

(62) Division of application No. 10/326,184, filed on Dec. 20, 2002, now Pat. No. 7,230,168.

(60) Provisional application No. 60/343,129, filed on Dec. 20, 2001.

(51) Int. Cl.
*C12N 15/82* (2006.01)
*C12N 15/53* (2006.01)
*A01H 1/02* (2006.01)
*A01H 5/00* (2006.01)
*A01H 5/10* (2006.01)

(52) U.S. Cl. ........ 800/303; 800/274; 800/275; 800/278; 800/287; 800/320.1; 435/189

(58) Field of Classification Search .................. None
See application file for complete search history.

(56) References Cited

U.S. PATENT DOCUMENTS

| | | |
|---|---|---|
| 5,073,676 A | 12/1991 | Bridges |
| 5,086,169 A | 2/1992 | Mascarenhas |
| 5,107,065 A | 4/1992 | Shewmaker |
| 5,470,359 A | 11/1995 | Huffman |
| 5,477,002 A | 12/1995 | Tuttle et al. |
| 5,545,546 A | 8/1996 | Allen et al. |
| 5,569,831 A | 10/1996 | DellaPenna |
| 5,589,610 A | 12/1996 | De Beuckeleer et al. |
| 5,639,948 A | 6/1997 | Michiels et al. |
| 5,659,124 A | 8/1997 | Crossland et al. |
| 5,689,049 A | 11/1997 | Cigan et al. |
| 5,689,051 A | 11/1997 | Cigan et al. |
| 5,704,160 A | 1/1998 | Bergquist et al. |
| 5,706,603 A | 1/1998 | Bergquist et al. |
| 5,763,243 A | 6/1998 | Cigan et al. |
| 5,792,853 A | 8/1998 | Cigan et al. |
| 5,795,753 A | 8/1998 | Cigan et al. |
| 5,824,542 A | 10/1998 | Crossland et al. |
| 5,837,851 A | 11/1998 | Cigan et al. |
| 5,880,331 A | 3/1999 | Krebbers |
| 5,955,653 A | 9/1999 | Scott |
| 5,962,769 A | 10/1999 | Albertsen |
| 5,977,433 A | 11/1999 | Williams |
| 5,977,453 A * | 11/1999 | Boerboom ............... 800/320.1 |
| 6,005,167 A | 12/1999 | Van Tunen |
| 6,008,437 A | 12/1999 | Krebbers |
| 6,013,859 A | 1/2000 | Fabijanski |
| 6,018,104 A | 1/2000 | Koziel |
| 6,025,546 A | 2/2000 | Michiels |
| 6,037,523 A | 3/2000 | Albertsen |
| 6,072,102 A | 6/2000 | Cigan |
| 6,077,991 A | 6/2000 | Poovaiah |
| 6,207,883 B1 | 3/2001 | Baudot |
| 6,229,066 B1 | 5/2001 | Morris |
| 6,258,999 B1 | 7/2001 | Tomes |
| 6,617,497 B1 | 9/2003 | Morris |

FOREIGN PATENT DOCUMENTS

| | | |
|---|---|---|
| EP | 0271988 B1 | 6/1988 |
| EP | 0344029 B1 | 11/1989 |
| WO | 8910396 A1 | 11/1989 |
| WO | 9213956 A1 | 8/1992 |
| WO | 9213957 A1 | 8/1992 |
| WO | 9429465 A1 | 12/1994 |
| WO | 9904023 A1 | 1/1999 |
| WO | WO 99/06571 * | 2/1999 |
| WO | 9946396 A2 | 9/1999 |
| WO | 0049035 A1 | 8/2000 |

OTHER PUBLICATIONS

Ahokas, H., "Cytoplasmic Male Sterility in Barley: Evidence for the Involvement of Cytokinins in Fertility Restoration." Proc. Natl. Acad. Sci. USA, 1982, pp. 7605-7608, vol. 79, No. 24.
Alexander, M.P., "Differential Staining of Aborted and Nonaborted Pollen." Stain Technology, 1969, pp. 117-122, vol. 44, No. 3.
Armstrong D.J., "Cytokinin Oxidase and the Regulation of Cytokinin Degradation." Cytokinins Chemistry, Activity, and Function, 1994, pp. 139-154, CRC Press, US.
Becker et al., "Fertile Transgenic Wheat from Microprojectile Bombardment of Scutellar Tissue." the Plant Journal, 1994, pp. 299-307, vol. 5, No. 2. Bilyeu et al., "Molecular and Biochemical Characterization of a Cytokinin Oxidase from Maize." Plant Physiology, 2001, pp. 378-386, vol. 125, No. 1.
Bower et al., "Transgenic Sugarcane Plants via Microprojectile Bombardment." The Plant Journal, 1992, pp. 409-416, vol. 2, No. 3.
Bytebier et al., "T-DNA Organization in Tumor Cultures and Transgenic Plants of the Monocotyledon Asparagu officinalis." Pro. Natl. Acad. Sci. USA, 1987, pp. 5345-5349, vol. 84, No. 15.
Carpin et al., "Changes of Both Polypeptide Pattern and Sensitivity to Cytokinin Following Transformation of Periwinkle Tissues with the Isopentenyl Transferase Gene," Plant Physio and Biochem, 1997, pp. 603-609, vol. 35, No. 8.
Casas et al., "Transgenic Sorghum Plants via Microprojectile Bombardment." Proc. Natl. Acad. Sci. USA, 1993, pp. 11212-11216, vol. 90, No. 23.
Cech, T., "Ribozymes and Their Medical Implications." JAMA, 1988, pp. 3030-3034, vol. 260, No. 20.
Christou P., "Genetic Engineering of Crop Legumes and Cereals: Current Status and Recent Advances." Argo-Food-Industries Hi-Tech, 1994, pp. 17-27.

(Continued)

Primary Examiner — David T Fox
(74) Attorney, Agent, or Firm — Senniger Powers LLP

(57) ABSTRACT

Methods for the production of reversibly male-sterile plants by introduction of a polynucleotide encoding a cytokinin oxidase are disclosed along with nucleic acid constructs and transformed cells useful in the production of such plants. Also disclosed is the use of plants containing recombinant nucleic acid sequences in preventing pollination of plants with pollen containing one or more transgenes and in the introduction of economically important traits into elite varieties of plants.

18 Claims, 6 Drawing Sheets

OTHER PUBLICATIONS

Christou P., "Production of Transgenic Rice (*Oryza sativa* L.) Plants from Agronomically Important Indica and Japonica Varieties via Electric Discharge Particle Acceleration of Exogenous DNA Into Immature Zygotic Embryos." Bio/Technology, 1991, pp. 957-962, vol. 9, No. 10.

de la Pena, et al., "Transgenic Rye Plants Obtained by Injecting DNA Into Young Floral Tillers." Nature, 1987, pp. 274-276, vol. 325.

Dellaporta et al., "The Sex Determination Process in Maize." Science, 1994, pp. 1501-1505, vol. 266, No. 5190.

Eenink et al., "Anatomical Changes in Flower Buds of Lettuce (*Lactuca sativa* L.) Treated with a GA3-Solution for Induction of Male Sterility." Acta Bot. Neerl., 1978, pp. 199-204, vol. 27, No. 3/4.

Fang et al., "Multiple cis Regulatory Elements for Maximal Expression of the Cauliflower Mosaic Virus 35S Promoter in Transgenic Plants." The Plant Cell, 1989, pp. 141-150, vol. 1, No. 1.

Fisk et al., "The Introduction and Expression of Transgenes in Plants." Scientia Horticulturae, 1993, pp. 5-36, vol. 55, Nos. 1-2.

Fromm et al., "Inheritance and Expression of Chimeric Genes in the Progeny of Transgenic Maize Plants." Bio/Technology, 1990, pp. 833-839, vol. 8, No. 9.

Gasser et al., "Genetically Engineering Plants for Crop Improvement." Science, 1989, pp. 1293-1299, vol. 244, No. 4910.

Gordon-Kamm et al., "Transformation of Maize Cells and Regeneration of Fertile Transgenic Plants." The Plant Cell, 1990, pp. 603-618, vol. 2.

Green et al., "The Role of Antisense RNA in Gene Regulation." Ann. Rev. Biochem., 1986, pp. 569-597, vol. 55.

Guerrero et al., "Promoter Sequences from a Maize Pollen-Specific Gene Direct Tissue-Specific Transcription in Tobacco." Mol. Gen. Genet., 1990, pp. 161-168, vol. 224, No. 2.

Hamilton et al., "Characterization of a Pollen-Specific Genomic Clone from Maize." Sex Plant Reprod., 1989, pp. 208-212, vol. 2.

Hanson et al., "Characterization of a Pollen-Specific cDNA Clone from Zea mays and its Expression." The Plant Cell, 1989, pp. 173-179, vol. 1.

Hare et al., "Inhibitory Effect of Thidiazuron on the Activity of Cytokinin Oxidase Isolated from Soybean Callus." Plant Cell Physiol., 1994, pp. 1121-1125, vol. 35, No. 8.

Hartley, R.W., "Barnase and Barstar Expression of its Cloned Inhibitor Permits Expression of a Cloned Ribonuclease." J. Mol. Biol. 1988, pp. 913-915, vol. 202, No. 4.

Herskowitz, I., "Functional Inactivation of Genes by Dominant Negative Mutations." Nature, 1987, pp. 219-222, vol. 329, No. 6136.

Hird et al., "The Anther-Specific Protein Encoded by the Brassica napus and Arabidopsis thaliana A6 Gene Displays . Similarity to β-1,3-glucanases." The Plant Journal, 1993, pp. 1023-1033, vol. 4, No. 6.

Horn et al., "Transgenic Plants of Orchardgrass (*Dactylis glomerata* L.) from Protoplasts." Plant Cell Reports, 1988, pp. 469-472, vol. 7, No. 7.

Houba-Herin et al., "Cytokinin Oxidase from Zea mays: Purification, cDNA Cloning and Expression in Moss Protoplasts." The Plant Journal, 1999, pp. 615-626, vol. 17, No. 6.

Huang, "Transgenic Studies on the Involvement of Cytokinin and Gibberellin in Male Development," Plant Physiology, 2003, pp. 1270-1282, vol. 131, No. 3.

Hunter et al., "Inbred Maize Performance Following Tassel and Leaf Removal." Agronomy Journal, 1973, pp. 471-472, vol. 65, No. 3.

Ishida et al., "High Efficiency Transformation of Maize (*Zea mays* L.) Mediated by Agrobacterium tumefaciens." Nature Biotechnology, 1996, pp. 745-750; vol. 14.

Koltunow et al., "Different Temporal and Spatial Gene Expression Patterns Occur During Anther Development." The Plant Cell, 1990, pp. 1201-1224, vol. 2.

Koziel et al., "Field Performance of Elite Transgenic Maize Plants Expressing an Insecticidal Protein Derived from *Bacillus thuringiensis*." Bio/Technology, 1993, pp. 194-200, vol. 11, No. 2.

Lagna et al., "Use of Dominant Negative Constructs to Modulate Gene Expression." Current Topics in Developmental Biology, 1998, pp. 75-98, vol. 39.

Li et al., "Locus Control Regions, Coming of Age at a Decade Plus." Trends in Genetics, 1999, pp. 403-408, vol. 15, No. 10.

Louis J-P., "Cytokins and Differentiation Processes in Mercurialis Annua," Plant Physiology, 1990, pp. 1535-1541, vol. 94.

Luo et al., "A Simple Method for the Transformation of Rice Via the Pollent-Tube Pathway." Plant Molecular Biology Reporter, 1989, pp. 69-77, vol. 7, No. 1.

McCormick, S., "Molecular Analysis of Male Gametogenesis in Plants." Trends in Genetics, 1991, pp. 298-303, vol. 7, No. 9.

Meinkoth et al., "Hybridization of Nucleic Acids Immobilized on Solid Supports." Analytical Biochemistry, 1984, pp. 267-284, vol. 138, No. 2.

Moore, J., "Male Sterility Induced in Tomato by Sodium 2,3-Dichloroisobutyrate." Science, 1959, pp. 1738-1740, vol. 129, No. 3362.

Morris et al., "Isolation of a Gene Encoding a Glycosylated Cytokinin Oxidase from Maize." Biochemical and Biophysical Research Communications, 1999, pp. 328-333, vol. 255, No. 2.

Morris, R. Accession No. AR150951, Aug. 2001.

Morris, R. Accession No. AR399210, Dec. 2003.

Paul et al., "The Isolation and Characterization of the Tapetum-Specific *Arabidopsis thaliana* A9 Gene." Plant molecular Biology, 1992, pp. 611-622, vol. 19, No. 4.

Potrykus, I., "Gene Transfer to Plants: Assessment of Published Approaches and Results." Annu. Rev. Plant Physiol. Plant Mol. Biol., 1991, pp. 205-225, vol. 42.

Rastogi et al., "In Vitro Development of Angiosperm Floral Buds and Organs." Plant Cell, Tissue and Organ Culture, 1989, pp. 145-174, vol. 16, No. 3.

Rhodes et al., "Genetically Transformed Maize Plants from Protoplasts." Science, 1988, pp. 204-207, vol. 240.

Russel et al., "Differential Expression and Sequence Analysis of the Maize Glyceraldehyde-3-Phosphate Dehydrogenase Gene Family." The Plant Cell, 1989, pp. 793-803, vol. 1, No. 8.

Saini et al., "Sterility in Wheat (*Triticum aestivum* L) Induced by Water Deficit or High Temperature: Possible Mediation by Abscisic Acid." Aust. J. Plant. Physiol, 1982, pp. 529-537, vol. 9, No. 5.

Sawhney V.K., "The Role of Temperature and its Relationship with Gibberellic Acid in the Development of Floral Organs of Tomato (*Lycopersicon esculentum*)." Canadian Journal of Botany, 1983, pp. 1258-1265, vol. 61,. No. 4.

Sawhney et al., "Male Sterility in Flowering Plants: Are Plant Growth Substances Involved?" American Journal of Botany, 1994, pp. 1640-1647, vol. 81, No. 12.

Sekhar et al., Role of ABA in Stamen and Pistil Development in the Normal and Solanifolia Mutant of Tomato (*Lycopersicon esculentum*). Sex Plant Repord, 1991, pp. 279-283, vol. 4.

Seurinck et al., "The Nucleotide Sequence of an Anther-Specific Gene." Nucleic Acids Research, 1990, p. 3403, vol. 18, No. 11.

Shen et al., "Brassica Anther-Specific Genes: Characterization and in Situ Localization of Expression." Mol. Gen. Genet., 1992, pp. 379-389, vol. 234, No. 3.

Shukla et al., "Metabolism of Dihydrozeatin in Floral Buds of Wild-Type and Genic Male Sterile Line of Rapeseed (*Brassica napus* L.)." Journal of Experimental Botany, 1993, pp. 1497-1505, vol. 44, No. 266..

Singh et al., "Cytokinins in a Normal Line and the Ogura (ogu) Cytoplasmic Male-Sterile Line of Rapeseed (*Brassica napus*)," Plant Science, 1992, pp. 147-154, vol. 86.

Singh et al., "Endogenous Hormones in Seeds, Germination Behaviour and Early Seedling Characteristics in a Normal and ogura Cytoplasmic Male Sterile Line of Rapeseed (*Brassica napus* L.)," J Exp Botany, 1992, pp. 1497-1505, vol. 43, No. 256.

Smith et al., Antisense RNA Inhibition of Polygalacturonase Gene Expression in Transgenic Tomatoes. Nature, 1988, pp. 724-726, vol. 334, No. 6184.

Smith et al., "Inheritance and Effect on Ripening of Antisense Polygalacturonase Genes in Transgenic Tomatoes." Plant Molecular Biology, 1990, pp. 369-379, vol. 14, No. 3.

Somers et al., "Fertile, Transgenic Oat Plants." BiolTechnology, 1992, pp. 1589-1594, vol. 10, No. 12.

Toriyama et al., "Transgenic Rice Plants After Direct Gene Transfer Into ProtoPlasts." Bio/Technology, 1988, pp. 1072-1074, vol. 6.

van der Meer et al., "Antisense Inhibition of Flavonoid Biosynthesis in Petunia Anthers Results in Male Sterility." The Plant Cell, 1992, pp. 253-262, vol. 4, No. 3.

Vasil et al., "Herbicide Resistant Fertile Transgenic Wheat Plants Obtained by Microprojectile Bombardment of Regenerable Embryogenic Callus." BiolTechnology, 1992, pp. 667-674, vol. 10, No. 6.

Wan et al., "Generation of Large Numbers of Independently Transformed Fertile Barley Plants." Plant Physiol., 1994, pp. 37-48, vol. 104, Nos. 1-4.

Wang et al., "Transgenic Plants of Tall Fescue (Festuca Arundinacea Schreb.) Obtained by Direct Gene Transfer to Protoplasts." Bio/Technology, 1992, pp. 691-696, vol. 10, No. 6.

Waterhouse et al., "Virus Resistance and Gene Silencing in Plants can be Induced by Simultaneous Expression of Sense and Antisense RNA." Proc. Natl. Acad. Sci, USA, 1998, pp. 13959-13964, vol. 95, No. 23.

Weeks et al., "Rapid Production of Multiple Independent Lines of Fertile Transgenic Wheat (*Triticum aestivum*)." Plant Physiol, 1993, pp. 1077-1084, vol. 102, Nos. 1-4.

Weigel et al., "Activation Tagging in Arabidopsis." Plant Physiology, 2000, pp. 1003-1013, vol. 122, No. 4.

Werner et al., "Regulation of Plant Growth by Cytokinin." PNAS, 2001, pp. 10487-10492, vol. 98, No. 18.

Weterings et al., "Characterization of a Pollen-Specific cDNA Clone from *Nicotiana tabacum* Expressed During Microgametogenesis and Germination." Plant Molecular Biology, 1992, pp. 1101-1111, vol. 18, No. 6.

Williams et al., "Male Sterility Through Recombinant DNA Technology." Pollen Biotechnology for Crop Production and Improvement, 1997, pp. 237-257, Cambridge University Press, US.

Ye et al., "Arabidopsis Ovule is the Target for Agrobacterium in planta Vacuum Infiltration Transformation." The Plant Journal, 1999, pp. 249-257, vol. 19, No. 3.

Zhang et al., "Efficient Regeneration of Transgenic Plants from Rice Protoplasts and Correctly Regulated Expression of the Foreign Gene in the Plants." Theor Appl Genet, 1988, pp. 835-840, vol. 76, No. 6.

Zhang et al, "Transgenic Rice Plants Produced by Electroporation-Mediated Plasmid Uptake into Protoplasts." Plant Cell Reports, 1988, pp. 379-384, vol. 7, No. 6.

Zhong et al., "Transgenic Plants of Turfgrass (*Agrostis palustris* Huds.) from Microprojectile Bombardment of Embryogenic Callus." Plant Cell Reports, 1993, pp. 1-6, vol. 13., No. 1.

\* cited by examiner

REVERSIBLE MALE STERILITY IN TRANSGENIC PLANTS BY EXPRESSION OF CYTOKININ OXIDASE

CROSS-REFERENCE TO RELATED APPLICATIONS

This application is a divisional of application Ser. No. 10/326,184, filed Dec. 20, 2002, now U.S. Pat. No. 7,230,168, which claims the benefit of provisional application Ser. No. 60/343,129, filed Dec. 20, 2001, each of which is hereby incorporated herein by reference in its entirety.

FIELD OF THE INVENTION

The current invention generally relates to a method for the production of reversible male sterility in transgenic plants. The method comprises transforming a plant cell with a nucleic acid construct encoding cytokinin oxidase where expression of the cytokinin oxidase inhibits pollen formation or male organ development in the plant. Fertility restoration in the plant is achieved by restoration of normal cytokinin levels.

BACKGROUND

Reversible male sterility is a valuable trait in the production of hybrid seed. Since phytohormones are believed to be involved in the plant male organ development, male sterility can potentially be induced by alteration of endogenous hormone levels. Several attempts have been made to chemically induce male sterility with the application of phytohormones (Moore, *Science,* 129:1738-1740, 1959; Eeninck et al., *Acta Bot. Neerla,* 27:199-204, 1978; Sawhney, *Can. J. Botany,* 61:1258-1265, 1981; Saini et al., *Aust. J. Plant Physiol.,* 9:529-537, 1974; Chandra Sekhar et al., *Sex. Plant Reprod.,* 4:279-283, 1991). Although these exogenous hormone treatments successfully produced male sterile plants, the narrow window of application, the necessity of applying chemicals continuously to produce sterility, lower seed yields on the treated plants after crossing, and occasional lapses in achieving complete sterility make hormonal induction of male sterility impractical for commercial hybrid seed production. The pleiotropic effects of the hormone applications as well as environmental influences on exogenous hormone uptake, translocation and metabolism likely cause these inconsistencies.

The discovery of genes involved in hormone pathways and promoters conferring tissue specific expression, permit control of endogenous phytohormone levels in specific tissues, and allow precise, effective induction of male sterility. More importantly, male sterility induced by phytohormone perturbations can theoretically be reversed by application of the appropriate phytohormonal agonists or antagonists. Fertility restoration is critical as it enables inbred male sterile lines to be maintained.

The use of molecular biology to produce male sterility in plants has been described. In a series of patents, Cigan et al. disclose the use of the anther-specific promoter 5126 and variants thereof to control expression of sequences related to pollen formation (U.S. Pat. Nos: 5,689,049; 5,689,051; 5,763,243; 5,792,853; 5,795,753; 5,837,851; and 6,072,102). Albertson et al. (U.S. Pat. No. 5,962,769) describe a method for producing reversible male-sterile plants by introduction of an expression vector which produces avidin. Male sterility is reversed by crossing to a "restorer" line expressing anti-sense avidin or a suitable ribozyme. Alternatively, sterility can be reversed by application of biotin. Baudot et al. (U.S. Pat. No.: 6,207,883 B1) disclose the male fertility gene Ms41-A in *Arabidopsis* and a related maize gene Zm41-A. Baudot et al. further disclose that mutation of the Ms41-A gene resulted in male sterility. Michiels et al. (U.S. Pat. No. 6,025,546) utilized a method of transforming plants with a coregulating gene combined with a male sterility gene to generate a higher frequency of male sterile transgenic plants. Poovaiah et al. (U.S. Pat. No. 6,077,991) disclose the suppression of calcium/calmodulin-dependant protein kinase expression by the use of antisense constructs to induce male-sterility. Scott et al. (U.S. Pat. No. 5,955,653) disclose the use of a tapetum-specific callase gene and its promoter to induce male-sterility. Van Tunen et al. (U.S. Pat. No. 6,005,167) disclose a method for inducing male sterility by the use of recombinant polynucleotides that inhibit the expression of one or more gene involved in the synthesis of chalcone or one of its precursors.

SUMMARY OF THE INVENTION

Among the several aspects of the invention is provided a method for producing a plant characterized by reversible male-sterility comprising transforming a plant cell with a construct containing a polynucleotide encoding a cytokinin oxidase and regenerating a plant from the plant cell wherein expression of the cytokinin oxidase inhibits pollen formation or male organ development in the plant and restoration of male-fertility is possible by restoration of normal cytokinin levels. Restoration of normal cytokinin levels can be achieved by application of cytokinin, a cytokinin oxidase inhibitor, or any combination thereof.

In one aspect, the construct further comprises a regulatory sequence and a termination sequence, both operably linked to a polynucleotide encoding the cytokinin oxidase. In another aspect, the regulatory sequence comprises a promoter. Suitable promoters can be selected from promoters that are constitutive, inducible, environmentally-regulated, developmentally-regulated, organelle-specific, cell-specific, tissue-specific, male specific, anther-specific, pollen-specific, stamen-specific, tapetum-specific or any combination thereof, for example, an inducible, male-specific promoter.

In a further aspect, the method further comprises transforming the plant cell containing a polynucleotide encoding a cytokinin oxidase with at least one additional nucleic acid construct comprising an inducible promoter and a transcription termination sequence both operably linked to a polynucleotide encoding a cytokinin biosynthesis enzyme active in the plant. In an alternative aspect, the male sterile plant is produced by sexually crossing a plant comprising a polynucleotide encoding a cytokinin oxidase with a plant, typically of the same variety, comprising at least one nucleic acid construct containing an inducible promoter and a transcription termination sequence both operably linked to a polynucleotide encoding a cytokinin biosynthesis enzyme active in the variety. In either case, male-fertility can be restored in the resulting plant by expression of the cytokinin biosynthesis enzyme(s).

In yet another aspect, the method further comprises transforming the plant cell comprising the construct encoding a cytokinin oxidase with an additional nucleic acid construct comprising an inducible promoter and a transcription termination sequence both operably linked to an antisense construct expression of which suppresses expression of the cytokinin oxidase. Alternatively, a male-sterile plant is produced by sexually crossing a plant comprising a nucleic acid construct containing a polynucleotide encoding a cytokinin oxidase with a plant, typically of the same variety, comprising a nucleic acid construct containing an inducible promoter and a transcription termination sequence both operably linked to an antisense construct expression of which suppresses expression of the cytokinin oxidase. In either case, male-fertility can be restored by expression of the antisense construct.

In another embodiment, the method further comprises transforming the plant cell comprising the construct encoding a cytokinin oxidase with an additional nucleic acid construct comprising an inducible promoter and a transcription termination sequence both operably linked to a polynucleotide encoding a dominant negative mutant protein expression of which decreases expression or activity of the cytokinin oxidase. Alternatively, a male-sterile plant is produced by sexually crossing a plant comprising a nucleic acid construct containing a polynucleotide encoding a cytokinin oxidase with a plant, typically of the same variety, comprising a nucleic acid construct containing an inducible promoter and a transcription termination sequence both operably linked to a polynucleotide encoding a dominant negative mutant protein, expression of which decreases expression or activity of the cytokinin oxidase. In either case, male-fertility can be restored by expression of the dominant negative mutant protein.

Additional aspects include seeds from plants produced by any of the preceding methods, uniform populations of plants produced by any of the preceding methods, and hybrid plants produced by crossing plants produced by any of the preceding methods with plants of a different variety.

Other features and aspects of the invention are described in more detail below.

BRIEF DESCRIPTION OF THE DRAWINGS

These and other features, aspects, and advantages of the present invention will become better understood with regard to the following description, appended claims and accompanying figures where:

ABBREVIATIONS AND DEFINITIONS

Figure 1A:
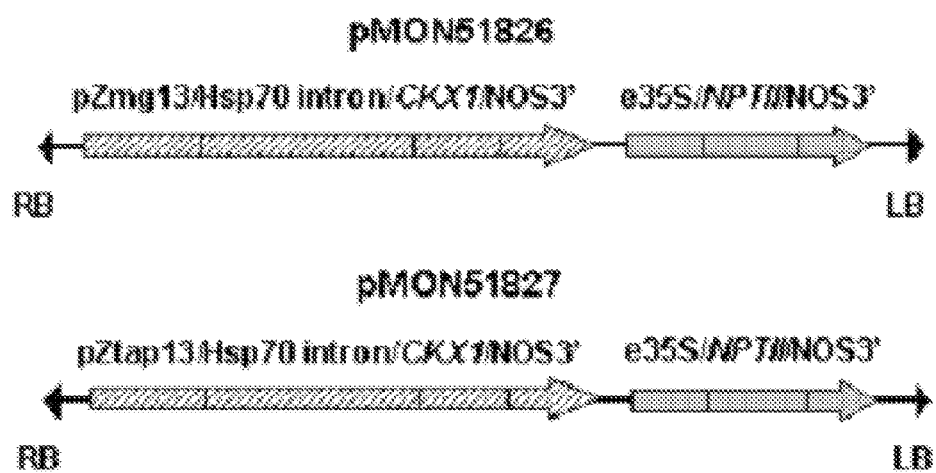
FIGS. 1A-1B. (A) depicts T-DNA regions of pMON51826 and p MON51827. (B) depicts R0 transgenic plants of pMON51827 (S16400 and S16409) and pMON51826 (S16802, S16825, and S16832). All of the transgenic male sterile tassels shown in the figure are enlarged.

To facilitate understanding of the invention, a number of terms and abbreviations as used herein are defined below:

As used herein, the term "amino acid" is used in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids such as norleucine, ornithine, etc.; and chemically synthesized compounds having properties known in the art to be characteristic of amino acids.

As used herein in reference to cytokinin oxidase, the term "biological activity" refers to the ability of the particular cytokinin oxidase to oxidatively remove cytokinin side chains to give adenine and the corresponding isopentenyl aldehyde. Also, as used herein, "cytokinin oxidase" and "cytokinin dehydrogenase" are used interchangeably.

As used herein, the terms "complementary" or "complementarity" refer to the pairing of bases, purines and pyrimidines, that associate through hydrogen bonding in double stranded nucleic acid. The following base pairs are complementary: guanine and cytosine; adenine and thymine; and adenine and uracil. The terms as used herein the terms include complete and partial complementarity.

As used herein, the term "hybridization" refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Thus the term contemplates partial as well as complete hybridization. Such techniques and conditions are well known to practitioners in this field.

As used herein the term "linkage" refers to the situation in which two genes or segments of DNA are inherited together. Linked genes or DNA segments are located on the same chromosome and are generally located within 50 centiMorgans (cM) of each other. As used herein the term "linked" in reference to genes and DNA segments means that the genes and/or segments are located on the same chromosome within 50 cM, typically 10 cm, more typically 2 cm and more typically still 0.1 cm of each other.

As used herein, "peptide" and "protein" are used interchangeably and mean a compound that consists of two or more amino acids that are linked by means of peptide bonds.

As used herein, "polynucleotide" and "oligonucleotide" are used interchangeably and mean a polymer of at least 2 nucleotides joined together by phosphodiester bonds and may consist of either ribonucleotides or deoxyribonucleotides.

As used herein, a "recombinant nucleic acid" is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequences derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design.

As used herein "recombinant protein" means that the protein, whether comprising a native or mutant primary amino acid sequence, is obtained by expression of a gene carried by a recombinant DNA molecule in a cell other than the cell in which that gene and/or protein is naturally found. In other words, the gene is heterologous to the host in which it is expressed. It should be noted that any alteration of a gene, including the addition of a polynucleotide encoding an affinity purification moiety to the gene, makes that gene unnatural for the purposes of this definition, and thus that gene cannot be "naturally" found in any cell.

As used herein "SDS" means sodium dodecyl sulfate.

As used herein, "secretion sequence" or "signal peptide or signal sequence" means a sequence that directs newly synthesized secretory or membrane proteins to and through membranes of the endoplasmic reticulum, or from the cytoplasm to the periplasm across the inner membrane of bacteria, or from the matrix of mitochondria into the inner space, or from the stroma of chloroplasts into the thylakoid. Fusion of such a sequence to a gene that is to be expressed in a heterologous host ensures secretion of the recombinant protein from the host cell.

As used herein, "sequence" means the linear order in which monomers occur in a polymer, for example, the order of amino acids in a polypeptide or the order of nucleotides in a polynucleotide.

As used herein "1×SSC" means 0.015 M NaCl/0.0015 M sodium citrate.

As used herein "1×SSPE" means 1.8 M NaCl, 10 mM NaH$_2$PO$_4$, 1 mM EDTA.

As used herein, "targeting sequence" means in the context of gene or polynucleotide insertion, a sequence which results in the gene or polynucleotide being inserted at a particular location by homologous recombination. In the context of proteins or peptides, "targeting sequence" refers to a nucleotide sequence encoding an amino acid sequence the presence of which results in a protein being directed to a particular destination within a cell.

As used herein, the term "transgenic" refers to a plant whose germline contains a gene or nucleic acid construct introduced using recombinant DNA technology. As used herein the term "transgene" means a gene or DNA construct which has been introduced into the germ line of a plant using recombinant DNA technology.

DESCRIPTION OF THE PREFERRED EMBODIMENTS

A method for producing plants with reversible male sterility has been discovered. These plants are produced by introducing polynucleotide constructs encoding a cytokinin oxidase, such as cytokinin oxidase 1 (CKX1). Male sterility in the transformed plants is due to expression and accumulation of cytokinin oxidase, which leads to a decrease in levels of cytokinin present in the plant. Because cytokinin is needed for normal pollen formation and male organ development, an increase in cytokinin oxidative degradation results in either a failure of normal pollen formation or a failure in male organ development. Male fertility can be restored by the restoration of normal cytokinin levels either by the application of natural or synthetic cytokinins, application of cytokinin oxidase inhibitors, inhibition of expression or activity of the introduced cytokinin oxidase, or any combination thereof.

Production of Transgenic Plants

Generally speaking, transgenic plants comprising cells containing isolated polynucleotides, vectors or expression cassettes of the present invention can be produced by transforming plant cells with a DNA construct as described herein via any of the foregoing methods; selecting plant cells that have been transformed on a selective medium; regenerating plant cells that have been transformed to produce differentiated plants; and selecting transformed plants that are male-sterile.

Any nucleic acid sequence encoding a cytokinin oxidase enzyme biologically active in the plant of interest can be used. The sequence used can be the coding region for the enzyme or can be a mutated and/or truncated form of the enzyme as long as the mutated and/or truncated form retains cytokinin oxidase activity. Polynucleotide sequences encoding cytokinin oxidase are known in the art and can be found, for example, in the GenBank data base maintained by the National Biotechnology Information Center available to the public at www.ncbi.nlm.nih.gov/ and the data bases maintained at the European Bioinformatics Institute and available to the public at www.ebi.ac.uk/. In addition, sequence data for cytokinin oxidase has been published by Morris et al. (*Biochim. Biophys. Res. Commun.*, 255:328-333) and Houba-Herin et al. (*Plant J.*, 17:615-626, 1999). In one embodiment, the polynucleotide encoding a *Zea maize* cytokinin oxidase 1 enzyme found in GenBank sequence accession no. AF044603 (SEQ ID NO: 1) may be used. In another embodiment, one of several polynucleotides encoding a *Glycine max* cytokinin oxidase found in GenBank sequence accession nos. BU926889 (SEQ ID NO: 13), BU084470 (SEQ ID NO: 14), BM528151 (SEQ ID NO: 15), BE330968 (SEQ ID NO: 16), AW830743 (SEQ ID NO: 17), BM143498 (SEQ ID NO: 18) or BG651837 (SEQ ID NO: 19) may be employed. In yet another embodiment, one of several polynucleotides encoding an *Arabidopsis thaliana* cytokinin oxidase found in GenBank sequence accession nos. AF303978(SEQ ID NO: 8), AF303979(SEQ ID NO: 9), AF303980(SEQ ID NO: 10), AF303981(SEQ ID NO: 11), AF303982(SEQ ID NO: 12), BT000179 (SEQ ID NO: 20), or AY091158 (SEQ ID NO: 21), may be employed. In still another embodiment, a polynucleotide encoding a *Hordeum vulgare* cytokinin oxidase found in GenBank sequence accession nos. AF540382 (SEQ ID NO: 22), or AF362472 (SEQ ID NO: 23) may be used. In yet a further embodiment, a polynucleotide encoding a *Triticum aestivum* cytokinin oxidase found in GenBank accession no. AF362471 (SEQ ID NO: 24) may be utilized.

Also included in the invention are polynucleotides that exhibit 90%, typically 92%, more typically 95%, and more typically, 98% sequence identity with SEQ ID NO: 1 or any of SEQ ID Nos: 8-24, or any of their complementary sequences. Such nucleotide sequences generally hybridize to the nucleic acid of SEQ ID NO: 1 or any of SEQ ID Nos: 8-24, or any of their complementary sequences under high stringency conditions. Generally speaking, hybridization procedures typically include initial hybridzation in 5×SSPE, 1-5× Denhardt's solution, 10-200 micrograms/ml denatured heterologous DNA, 0.5% SDS, at 50-68° C. for a time sufficient to permit hybridization (e.g. several hours to overnight) followed by two washes in 2×SSPE, 0.1% SDS at room temperature and two additional 15 minute washes in 0.1×SSPE, 0.1% SDS at 42° C. followed by detection of the hybridization products. Higher stringency washing can accomplished by at least one additional wash in 0.1% SSPE, 0.1% SDS at 55° C., more typically at 60° C., and more typically still at 65° C. High stringency hybridizations can also be carried out in 5×SSPE and 50% formamide at 42° C. followed by washing as described above (Meinkoth and Wahl, *Anal. Biochem*, 138: 267-284 (1984)). As is well known by those of ordinary skill in the art, SSC can be substituted for SSPE in the above examples so that, for instance, hybridization can be accomplished in 5×SSC in place of 5×SSPE. It is well known to those of ordinary skill in the art that different compositions can result in equal stringency conditions for hybridization depending on well known factors such as the concentration of Na$^+$, the percentage formamide, the temperature, the $T_m$ of the hybrid to be formed, and the composition of the hybrid, e.g. DNA-DNA, DNA-RNA, or RNA-RNA. Thus the invention also encompasses nucleotide sequence that hybridize under conditions equivalent to those described above.

The polynucleotide sequence used can also encode either a secreted or non-secreted form of cytokinin oxidase. Non-secreted forms of CKX can be produced from secreted forms by the removal of the part of the sequence encoding the transit peptide necessary for secretion. Alternatively, polynucleotides encoding CKX polypeptides that are not naturally secreted such as AtCKX5 (Bilyeu et al., *Pl. Physiol.,* 125: 378-386, 2001) can be used.

Nucleic acid constructs of the present invention can be part of vectors and in particular, expression vectors or expression cassettes. In plants, transformation vectors capable of introducing polynucleotides encoding a cytokinin oxidase are easily designed, and generally contain one or more DNA coding sequences of interest under the transcriptional control of 5' and 3' regulatory sequences. Such vectors generally comprise, operatively linked in sequence in the 5' to 3' direction, a promoter sequence that directs the transcription of a downstream heterologous structural DNA in a plant; optionally, a 5' non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding the protein. Plant transformation vectors also generally contain a selectable marker. Typical 5' to 3' regulatory sequences include a transcription initiation start site, a ribosome binding site, an RNA processing signal, a transcription termination site, and/or a polyadenylation signal. Vectors for plant transformation have been reviewed in Rodriguez et al. (1988) *Vectors: A Survey of Molecular Cloning Vectors and Their Uses*, Butterworths, Boston; Glick et al. (1993) *Methods in Plant Molecular Biology and Biotechnology* CRC Press, Boca Raton, Fla; and Croy (1993) In *Plant Molecular Biology Labfax*, Hames and Rickwood, Eds., BIOS Scientific Publishers Limited, Oxford, UK. Non-limiting examples of plant transformation vectors useful in the present invention include pMON51826 and pMON51827, shown in FIG. 1.

Promoters useful in the present invention include those that confer appropriate cellular and temporal specificity of expression. Such promoters include those that are constitutive, inducible, environmentally-regulated, developmentally-regulated, organelle-specific, cell-specific, tissue-specific, male specific, anther-specific, pollen-specific, stamen-specific, tapetum-specific or any combination of the preceding, for example an inducible, male-specific promoter. Such promoters are well known to those of ordinary skill in the art. An example of a male-specific regulatory region can be found in U.S. Pat. No. 6,037,523. Examples of anther-specific promoters and regulatory sequences are disclosed U.S. Pat. Nos. 6,072,102; 5,962,769; 5,837,851; 5,795,753; 5,639,948; 5,589,610; 5,477,002; 6,013,859; 5,659,124; and 5,824,542. Examples of pollen-specific promoters are disclosed in U.S. Pat. Nos. 5,412,085; 5,086,169; 5,545,546; 6,018,104; 5,977,433; 5,545,546; and 5,086,169. Additional disclosure of pollen-specific promoters can be found in MacCormick (*Trends Genet.,* 2:298-303, 1991), Hamilton et al. (*Sex. Plant Reprod.,* 2:208, 1989) Guerrero et al. (*Molec. Gen. Genet.,* 224:161-168, 1990), Weterings et al. (*Plant Molec. Biol.,* 18:1101-1111, 1992) and Shen et al. (*Molec., Gen. Genet.,* 234:379-389, 1992). Examples of tapetum-specific promoters and regulatory sequences can be found in U.S. Pat. Nos. 5,470,359; 5,639,948; 5,589,610; and European Patent No. 0,344,029. Further examples of tapetum-specific promoters and regulatory sequences can be found in Koltunow et al. (*Plant Cell,* 2:1201-1224, 1990), Hird et al. (*Plant J.,* 4:1023-1033, 1993), Paul et al. (*Plant Molec. Biol.,* 19:611-622, 1992), and Seurinck et al. (*Nucl. Acids Res.,* 18:3403, 1990). Examples of stamen-specific promoters can be found in U.S. Pat. Nos. 5,639,948; 5,589,610; 5,880,331; 6,025,546; European Patent No. 0,344,029; and PCT Publication Nos. WO92/13956 and WO92/13957. In one embodiment, the pollen-specific promoter pZmg13 (Hanson et al., *Plant Cell,* 1:173-170, 1989) is used. In another embodiment, the anther-specific promoter pZtap (PCT Publication WO99/46396) is used.

A variety of different methods can be employed to introduce polynucleotides into plant protoplasts, cells, callus tissue, leaf discs, meristems, etc., to generate transgenic plants. These methods include, for example, *Agrobacterium*-mediated transformation, particle gun delivery, microinjection, electroporation, polyethylene glycol-mediated protoplast transformation, liposome-mediated transformation, etc. (Potrykus *Annu. Rev. Plant Physiol. Plant Mol. Biol.* 42: 205, 1991; Maliga et al., *Methods in Plant Molecular Biology*, Cold Spring Laboratory Press, 1995).

One aspect of the invention encompasses introduction of the polynucleotide into a dicot. Specific methods for transforming a wide variety of dicots and obtaining transgenic plants are well documented in the literature (Gasser and Fraley, *Science* 244:1293, 1989; Fisk and Dandekar, *Scientia Horticulturae* 55:5, 1993; Christou, *Agro Food Industry Hi Tech*, p. 17, 1994;and the references cited therein).

Another aspect of the invention encompasses introduction of the polynucleotide into a monocot. Successful transformation and plant regeneration have been achieved in the monocots as follows: asparagus (*Asparagus officinalis*; Bytebier et al. (1987) *Proc. Natl. Acad. Sci. USA* 84: 5345); barley (*Hordeum vulgarae*; Wan and Lemaux (1994) *Plant Physiol.* 104: 37); maize (*Zea mays*; Rhodes et al. (1988) *Science* 240: 204; Gordon-Kamm et al. (1990) *Plant Cell* 2: 603; Fromm et al. (1990) *Bio/Technology* 8: 833; Koziel et al. (1993) *Bio/Technology* 11: 194); oats (*Avena sativa*; Somers et al. (1992) *Bio/Technology* 10: 1589); orchardgrass (*Dactylis glomerata*; Horn et al. (1988) *Plant Cell Rep.* 7: 469); rice (*Oryza sativa*, including indica and japonica varieties; Toriyama et al. (1988) *Bio/Technology* 6: 10; Zhang et al. (1988) *Plant Cell Rep.* 7: 379; Luo and Wu (1988) *Plant Mol. Biol. Rep.* 6: 165; Zhang and Wu (1988) *Theor. Appl. Genet.* 76: 835; Christou et al. (1991) *Bio/Technology* 9: 957); rye (*Secale cereale*; De la Pena et al. (1987) *Nature* 325: 274); sorghum (*Sorghum bicolor*; Cassas et al. (1993) *Proc. Natl. Acad. Sci. USA* 90: 11212); sugar cane (*Saccharum* spp.; Bower and Birch (1992) *Plant J.* 2: 409); tall fescue (*Festuca arundinacea*; Wang et al. (1992) *Bio/Technology* 10: 691); turfgrass (*Agrostis palustris*; Zhong et al. (1993) *Plant Cell Rep.* 13: 1); and wheat (*Triticum aestivum*; Vasil et al. (1992) *Bio/Technology* 10: 667; Weeks et al. (1993) *Plant Physiol.* 102: 1077; Becker et al. (1994) *Plant J.* 5: 299).

Restoration of Male Fertility

Fertility can be restored in male-sterile lines by the restoration of normal cytokinin levels. By normal cytokinin levels is meant those levels of cytokinin that would be found in plants that are identical in their genetic make-up except for the presence of the exogenous recombinant oxidase gene. Typically, any means that restores cytokinin levels in a particular plant may be utilized. By way of example, suitable methods for the restoration of normal cytokinin levels can be achieved by application of cytokinins, cytokinin oxidase inhibitors or a combination of cytokinins and cytokinin oxidase inhibitors.

Generally speaking, cytokinins used to restore fertility can be either naturally occurring or synthetic. Synthetic cytokinins include those made by recombinant DNA technology as well as those made by conventional chemical synthesis. Examples of suitable native or synthetic cytokinins include kinetin, zeatin, zeatin riboside, dihydrozeatin, trans-zeatin, cis-zeatin, trans-zeatin riboside, isopentenyladenine, isopentenyladenosine and benzyladenine. Cytokinins can be conveniently applied to large numbers of plants in the form of a spray. In addition to the cytokinin and a suitable diluent, the spray can also contain other ingredients such as a surfactant to increase uptake of the cytokinin. Cytokinin can be used in a single application or multiple applications can be used depending one the situation. Typically, the cytokinin is applied for the duration of time necessary to restore the desired degree of male fertility in the particular plant species. Of course, the duration of its application will vary considerably depending upon the cytokinin employed and its rate of application, the particular plant species and its stage of development, and the desired degree of fertility restoration. One skilled in the art can readily determine the appropriate amount of time to apply the cytokinin. Moreover, the cytokinin can be applied at the V4, V7 and/or the V10 stages of development (See, Ritchie et al., *How a Corn Plant Develops*, Herman, ed., Iowa State University Cooperative Extension Service, Ames, Iowa, 1997). In one embodiment, the synthetic cytokinin, kinetin, is applied at a rate ranging between about 1 mg/plant to about 200 mg/plant, typically between about 3 mg/plant to about 100 mg/plant to restore male fertility.

Alternatively, a cytokinin oxidase inhibitor such as a cytokinin oxidase 1 inhibitor, can be used to restore normal cytokinin levels by inhibiting the increased breakdown of cytokinin due to the presence of the recombinant cytokinin oxidase 1 gene. As with the use of cytokinin to restore fertility, the cytokinin oxidase inhibitor used can be a naturally occurring or synthetic inhibitor. In one embodiment, the cytokinin oxidase inhibitor is an urea derivative. Examples of suitable urea derivatives include diphenyl and phenyl-pyridyl ureas, thiazole and thiazinoyl ureas, trisubstituted ureas, and thioureas. In another embodiment, the cytokinin oxidase inhibitor is a substituted cytokinin homolog. Generally speaking, suitable substituted cytokinin homologs include those cytokinins that have the N-6 hydrogens blocked with a methyl, fluoro, trifluoromethyl, or any other alkyl or aryl substituent. In still another embodiment, the cytokinin oxidase inhibitor comprises thidiazuron (TDZ) (Hare et al., *Plant Cell Physiol.*, 35:1121-1125, 1994; Bilyeu et al., *Zea Mays Plant Physiol.*, 125:378-386, 2001). The cytokinin oxidase inhibitor may conveniently be applied as a spray, which in addition to a diluent, may contain other useful ingredients such as a surfactant to improve uptake. Moreover, the inhibitor can be applied in a single application or in multiple applications and can be applied at the V4, V7 and/or V10 stages of development. Like the application of the cytokinin, the cytokinin oxidase inhibitor is typically applied for the duration of time necessary to restore the desired degree of male fertility in the particular plant species. Of course, the duration of its application will vary considerably depending upon the cytokinin oxidase inhibitor employed and its rate of application, the particular plant species and its stage of development, and the desired degree of fertility restoration. One skilled in the art can readily determine the appropriate amount of time to apply the cytokinin oxidase inhibitor. By way of example, when the cytokinin oxidase inhibitor is TDZ, it is typically applied as a spray at a rate ranging from between about 1 mg/plant to about 50 mg/plant, more typically from between about 3 mg/plant to about 30 mg/plant.

In another embodiment, male fertility is restored by applying a combination of cytokinin and cytokinin oxidase inhibitor. For example, any combination of kinetin and TDZ within the ranges given for each above can be used. It is also contemplated that a cytokinin having cytokinin oxidase activity may also be employed to restore male fertility. As with application of either cytokinins or cytokinin oxidase inhibitors alone, combinations can be applied as single or multiple applications and at the V4, V7 and/or V10 stages of development.

Male fertility can also be restored by the use of a second recombinant construct (restorer construct) that inhibits or interferes with expression of the construct encoding the cytokinin oxidase. In one embodiment, the restorer construct is operably linked to an inducible promoter so that application of the proper stimulus to drive expression of the restorer construct can be used to restore male fertility.

In one embodiment, the restorer construct encodes an antisense sequence. Antisense sequences can be produced by reversing the orientation of the transcribed region of a gene or polynucleotide sequence whose suppression is desired. When operatively coupled to a suitable inducible transcriptional promoter such as discussed herein, a transcript of the antisense DNA strand is produced when desired to restore fertility. The production and use of antisense DNA is well known in the art and can be found, for example, in Green et al., (1986) *Annu. Rev. Biochem.* 55:569. The transcript of the antisense DNA is antisense RNA. Without being bound by theory, it is believed that an individual antisense RNA molecule may hybridize with a complementary "sense" mRNA molecule to form an RNA-RNA duplex. Such a duplex may prevent the sense mRNA molecule from, for example, being translated or binding to another nucleic acid such as DNA. The presence of RNA-RNA duplexes may also initiate a sequence-specific RNA degradation pathway with the antisense molecules and/ or the RNA-RNA duplexes playing a role in initiating the degradation pathway, and both sense and antisense molecules serving as specific targets for degradation. Waterhouse et al. (*Proc. Natl. Acad. Sci. USA*, 95:13959-13964, 1998) reported that the most efficient gene silencing was achieved in plants by simultaneous expression of sense and antisense RNA. Without being bound by theory, this efficiency is thought to be due to the formation of double stranded (ds) RNA. Thus the presence in plants of the present invention of sense and antisense constructs encoding cytokinin oxidase is thought to result in a high efficiency of cytokinin oxidase inhibition.

It is also contemplated that the antisense transcript need not encompass the entire sense sequence, but may be a fragment which hybridizes to only a portion of the sense RNA. The antisense transcript should be of sufficient length to allow specificity in binding to the target (sense) transcript. In general, the antisense transcript should be at least 10 bases long, more typically at least 20 bases long, although the presence of rare sequences may allow the use of shorter antisense transcripts. The use of this technology to suppress the expression of specific plant genes has been described, for example in European Patent Publication No 271988; U.S. Pat. Nos. 5,073,676, 5,107,065 and 5,569,831; PCT Publication WO 00/49035, Smith et al, (1988) *Nature*, 334, 724-726; and Smith et al, (1990) *Plant Mol. Biol.* 14, 369-380).

In yet another embodiment, male fertility may be achieved by the use of a restorer construct containing a dominant negative mutation. Expression of a restorer construct containing a dominant negative mutation generates a mutant transcript that, when coexpressed with the cytokinin oxidase, inhibits the action of the cytokinin oxidase transcript. Methods for the design and use of dominant negative constructs are well known in the art and can be found, for example, in Herskowitz, *Nature*, 329:219-222, 1987 and Lagna and Hemmati-Brivanlou, *Curr. Topics Devel. Biol.*, 36:75-98, 1998.

In still another embodiment, the restorer construct encodes a ribozyme that cleaves the recombinant cytokinin oxidase transcript. Ribozymes are catalytic RNA molecules that can promote specific biochemical reactions without the need for auxiliary proteins. Reactions catalyzed by ribozymes can be either intramolecular or intermolecular. Examples of intramolecular reactions are self-splicing or self-cleaving reactions while intermolecular reactions involve other RNA molecules as substrates and more closely approximate true enzymatic reactions where the enzyme is unchanged after each reaction. In the present method, ribozymes catalyzing intermolecular reactions are generally employed. The use of ribozymes to alter expression of genes is discussed in Cech, *J. Am. Med. Assoc.*, 260:3030-3034 (1988).

Uses of Reversible Male Sterility

Generally speaking, the method of the present invention may be advantageously employed as a means for generating and maintaining male sterility in any plant species and in hybrids of any species. The method not only reduces the expense of seed production for existing hybrid plants such as corn, but also makes it possible to produce hybrid varieties of traditionally non-hybrid crops.

Figure 5A:
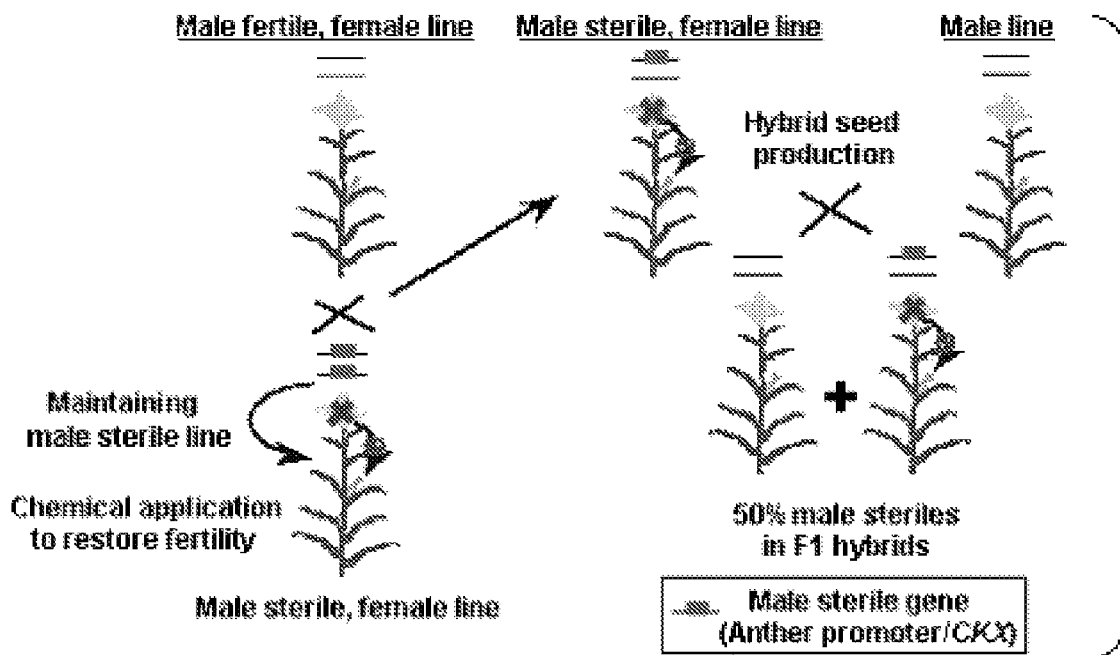
FIGS. 5A-5B detail the potential use of CKX-generated, reversible male sterility in hybrid seed production. (A) When expressed in anthers, the CKX gene is a dominant male-sterility gene that can be maintained as a homozygous female parental line by chemical fertility restoration. In the hybrid seed production fields, hemizygous plants derived from a cross between homozygous transgenic and isogenic wild type plants are used as females to produce F1 hybrids with 50% of them being fertile. (B) When the CKX gene is specifically expressed in pollen, only the transgenic plants that are homozygous for the transgene are male sterile. These male sterile transgenic plants can be maintained by kinetin and TDZ applications. When used in production, hemizygous fertile F1 hybrids are produced.

One aspect of the invention, therefore, encompasses use of the method to produce hybrid varieties having reversible male sterility in plants where hybrid varieties are traditionally employed in seed production. In one alternative of this embodiment, the plant is corn. By way of example, FIG. 5A outlines one embodiment to generate reversible male sterility in the production of hybrid corn employing the method of the invention. The method detailed in this example utilizes CKX linked to an anther specific promoter. When expressed in the anthers, CKX acts as a dominant male-sterility gene. Homozygous male-sterile female lines can be maintained, for example, by the use of chemical fertility restoration as described herein. The homozygous male-sterile female line is crossed with isogenic wild type plants to produce a hemizygous male-sterile female line. In hybrid seed production fields, the hemizygous line is crossed with a male line to produce F1 hybrid seeds. When planted, 50% of the resulting plants will be male-sterile, however, in species such as corn which produce an excess of pollen, the remaining 50% of the plants that are male fertile will provide sufficient pollen for pollination and thus normal yields. Furthermore, it has been suggested that out-crossed male sterile corn plants have a yield advantage over fertile plants due to resource reallocation from abolishing the development of male tissues (Hunter et al., *Agron. J.*, 65:471-472, 1973). Thus a hybrid population composed of 50% male steriles has the potential to deliver increased yields.

Figure 5B:
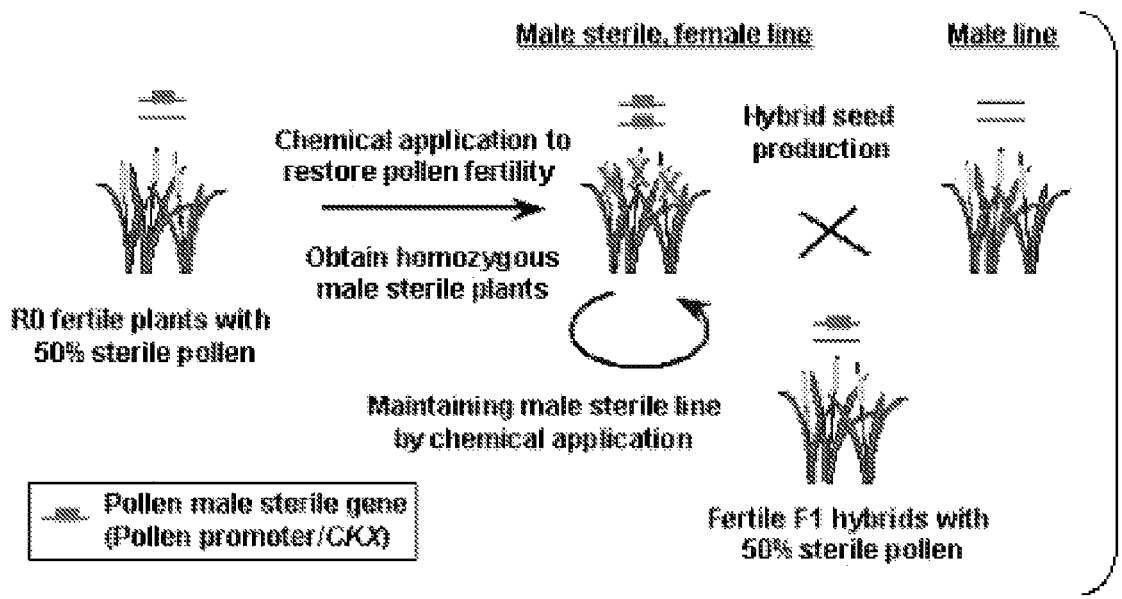

In yet another aspect, the method may be employed to produce hybrid varieties having reversible male sterility in plants where hybrid varieties are not traditionally utilized in seed production. Typical plants species where hybrid varieties are not employed in seed production include wheat, rice, canola and cotton. By way of example, FIG. 5B outlines one embodiment to generate reversible male sterility in the production of hybrid varieties in one of these plant species employing the method of the invention. In this example, expression of CKX is driven by a pollen-specific promoter, in which case only homozygous plants are male sterile. Homozygous male-sterile female lines are produced by selfing hemizygous lines and then the lines are maintained through restoration of male fertility, for example, by chemical restoration as described herein. The homozygous male-sterile female line is then crossed with a male line to produce F1 hybrid seed. This seed will result in fertile F1 hybrids with 50% sterile pollen.

In addition to the method for producing reversible male sterility in transgenic plants, plants produced by the method disclosed herein are also considered within the scope of the present invention. Such plants can be produced by the methods described above and contain a recombinant construct encoding a cytokinin oxidase. Optionally, the plant can further comprise a restorer construct such as those described above. Such plants can be either of the class dicotyledonae (dicots) or the class monocotyledonae (monocots). When first produced, the plant will be hemizygous for the introduced recombinant constructs. Such plants, however, can be made homozygous by "selfing" a technique which is well known in the art of plant breeding. Also within the scope of the present invention are uniform populations of plants which have been altered by the methods of the present invention such that they possess reversible male sterility.

Also included within the scope of the present invention are seeds and progeny from any of the above described plants. Another aspect of the present invention encompasses a method for the production of a hybrid plant comprising sexually crossing a plant having reversible male sterility and produced by the methods described herein with a plant of a different variety as well as the hybrid plants produced, uniform populations of such hybrid plants and seeds from such hybrid plants.

The present invention also provides a method for preventing or reducing cross-pollination of transgenic plants with wild type plants. With the increasing introduction of transgenic plants into production agriculture, there has been concern about the possible effects due to cross pollination between transgenic and wild type plants. Using the present methods, transgenic male sterile plants can be produced and planted together with a small number of non-transgenic plants to act as pollen donors. In this way, only wild type pollen would be released into the environment. By way of a non-limiting example, a transgenic hybrid plant combining insect resistance and an anther-expressed cytokinin oxidase, typically cytokinin oxidase 1, can be produced using the methods described herein. Interplanting with a small number of non-transgenic hybrids would provide a "refuge" for resistant management as well as pollen donors for complete pollination in the production field of the transgenic plants. Since the transgenic plants would be male-sterile, there would be no or greatly reduced pollination of wild type plants with transgenic pollen. As used herein in reference to cross-pollination "reduced" means that the incidence of pollination of wild type plants by transgenic pollen is less than occurs in the absence of an anther- or pollen-expressed cytokinin oxidase.

Similar results can be obtained using a plant which is hemizygous for a desirable transgene linked to a pollen-expressed cytokinin oxidase, typically a cytokinin oxidase 1. In this situation, only wild type pollen and not pollen producing the transgene linked to the expressed cytokinin oxidase would be produced. In one embodiment, the transgene and pollen expressed cytokinin oxidase are under the control of different regulatory sequences so that while the cytokinin oxidase is expressed primarily or typically only in pollen, the transgene is expressed in a wider variety of cell types. In this way, pollination of wild type plants with transgenic pollen can be avoided or reduced. Such plants can be produced by transforming plant cells with the linked transgene and pollen expressed cytokinin oxidase by any of the methods described herein, and regenerating a plant from said transformed cells. Alternatively, such plants can be produced by sexually crossing a plant homozygous for the linked transgene and pollen expressed cytokinin oxidase with a homozygous wild type (non-transgenic) plant to produce a hemizygous hybrid.

The present methods are also useful in the introduction of economically valuable traits from plants having, in general, undesirable production characteristics into plants having desirable characteristics (elite plants or varieties) and in particular elite hybrids. This method of introducing valuable traits is known as TopCrossing and is detailed in U.S. Pat. Nos. 5,704,160 and 5,706,603; both of which are herein incorporated by reference.

An example of the use of a TopCross can be found in corn. Most varieties of corn grown commercially are developed to meet common manufacturing and feeding requirements. There exists, however, a market for specialty varieties which differ from standard varieties by the presence of one or more economically important transgenic or non-transgenic traits. In corn, such traits include, but are not limited to, degree of starch branching, increased accumulation of sugars or water-soluble polysaccharides, degree of endosperm hardness, protein or amino acid content, and oil content. Unfortunately, many plants that possess these economically important traits also possess characteristics that make them agronomically undesirable. TopCross provides a means to circumvent this problem by capturing economically important traits from agronomically inferior plants through elite varieties. An elite variety, as is well known in the art, is a variety which possesses a favorable combination of traits making it particularly useful in commercial production.

In a TopCross, male-sterile plants of an elite variety are interplanted with a low density of male-fertile plants having the desired trait. By "low density" is meant that the male-fertile plants are interplanted at a rate which does not exceed about 10 male-fertile plants per 100 male-sterile plants. Due to low density planting, the presence of the agronomically inferior plants does not significantly reduce overall yields. The reversible male-sterility of the present invention is particularly useful in production of high value plants and grains by TopCross. For example, an agronomically elite variety, typically a hybrid variety, which has been made reversibly-male sterile by the methods of the present invention, can be randomly interplanted with an agronomically inferior variety which possesses a desirable trait and which is present in the field at a low density. The inferior variety is allowed to pollinate the elite variety allowing the economically important trait to be expressed in the plant and/or grain produced.

EXAMPLES

The following examples are intended to provide illustrations of the application of the present invention. The following examples are not intended to completely define or otherwise limit the scope of the invention.

Example 1

Vector Construction

The complete 1.7-kb corn cytokinin oxidase (CKX1)-containing DNA fragment including the transit peptide was inserted into expression cassettes driven by either the pollen-specific pZmg13 promoter (Hanson et al., *Plant Cell,* 1:173-179, 1989) or the anther-specific pZtap promoter (PCT Publ. No. WO 99/46396), and terminated by the nopline synthase sequence (NOS3'). These cassettes also included an intron from a heat shock protein (HSP70 intron) to increase the expression of CKX1. The resulting CKX1 expression cassettes were cloned into binary vectors using an enhanced CaMV 35S promoter (e35S)-driving NPTII as the selectable marker to generate pMON51826 and pMON51827 (FIG. 1A). All other genetic elements used in the binary vector were identical to those described by Ye et al (*Plant J.,* 19:249-257, 1999).

Example 2

Transformation, Plant Material and Growth Conditions

The binary vectors, pMON51826 and pMON51827 were electroporated into *Agrobacterium tumefaciens* ABI strain and introduced into corn embryos (LH198 X Hill) by *Agro-* bacterium-mediated transformation. H99 pollen was used to pollinate R0 male sterile transgenic plants to produce F1 seeds. All of the plants were grown in greenhouses at 28/21° C. (day/night) with a 16-hr photoperiod (400 mmol m$^{-2}$ sec$^{-1}$), and 50% relative humidity.

Figure 1B:
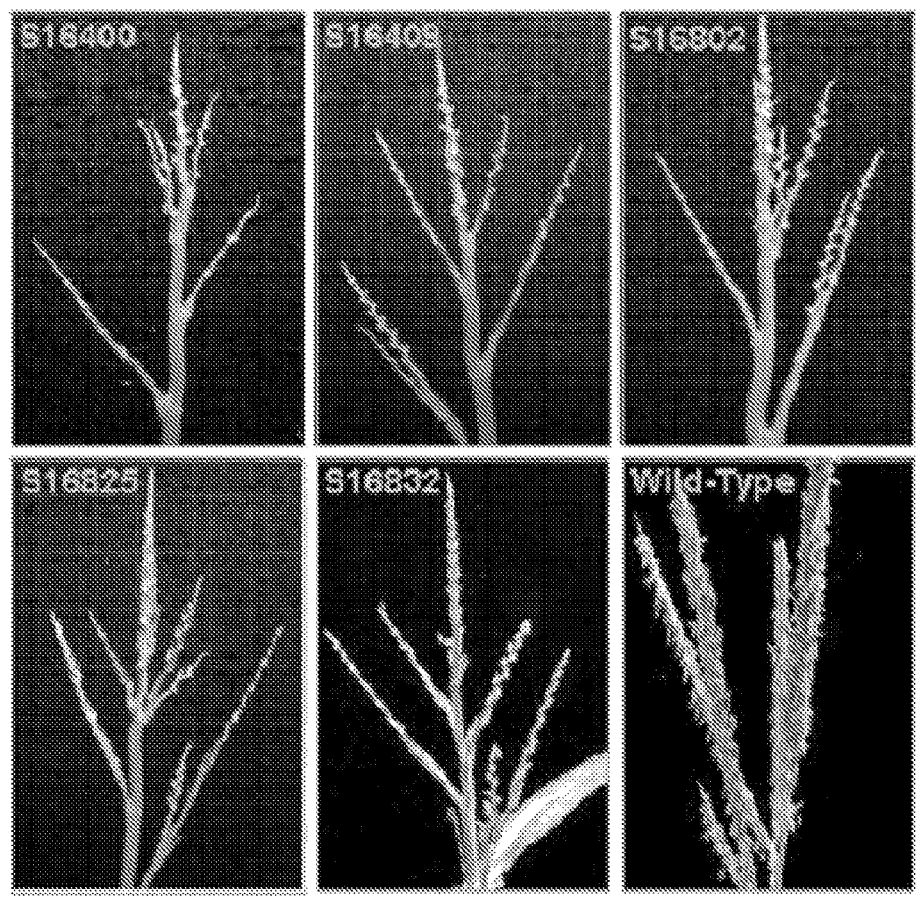

Thirty-three and 31 independent R0 transgenic plants were generated harboring pMON51826 and pMON51827, respectively. Despite the difference in the promoters, 29 plants each of pMON51826 and pMON51827 displayed a similar complete, sporophytic male sterile phenotype. At the apex of the plants where the tassels ordinarily form, the male sterile transgenic plants produced rudimentary terminal structures that lacked recognizable male florets or spikelets (FIG. 1B). These transgenic plants were also shorter and had narrower leaves than wild-type plants. Pollen from wild-type plants successfully fertilized several male sterile transgenic plants to yield F1 seeds. However, about half of the independently transformed CKX1 events did not produce fertile ears when out-crossed.

Example 3

Plant DNA Isolation and F1 Segregation Analysis

Figure 2A:
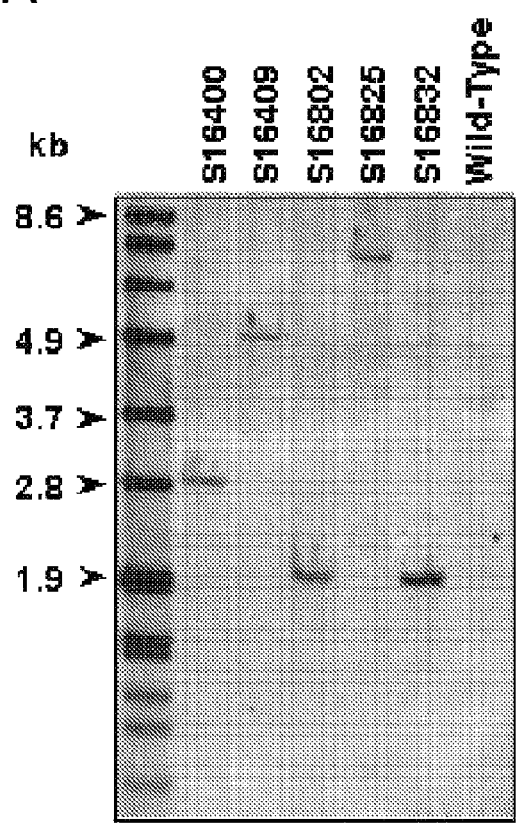
FIGS. 2A-2B depict genetic characterization of the transgenic lines. (A) DNA gel blot containing BamHI digests of genomic DNA isolated from leaves of lines S16400, S16409, S16802, S16825, S16832, and a wild type plant was hybridized with a NPTII probe. (B) The F1 plants resistant to kanamycin/paromomycin application and confirmed by a NPTII ELISA were scored as positives in the segregation analysis.

Five independent lines were selected for genomic DNA analysis (FIG. 2A). Genomic DNA was isolated from leaves of corn plants using the DNeasy Plant Mini Kit (Qiagen, Valencia, Calif.). Genomic DNA (20 mg) was digested with restriction enzymes (BamHI), separated on a 0.8% (w/v) agarose gel, and transferred to positively charged nylon membranes (Roche Molecular Biochemicals, Indianapolis, Ind.). Prehybridization, hybridization, washing and detection of the membranes were conducted using the non-radioactive DIG system (Roche Molecular Biochemicals) following the manufacturer's protocols.

The presence of NPTII in the F1 plants was determined by both antibiotic resistance and the NPTII ELISA from leaf protein extracts. An antibiotic solution containing 1 g/L kanamycin, 1 g/L paromomycin and 0.6% (v/v) Silwet L77 surfactant (Loveland, Greenley, Colo.), was applied to plants at V2 or V3 stages. Three days after application, the kanamycin susceptible plants began to display chlorosis symptoms on their leaves. The NPTII Pathoscreen Kit was purchased from Agdia (Elkhart, Ind.) and used for NPTII ELISAs following the manufacturer's protocol.

Figure 2B:
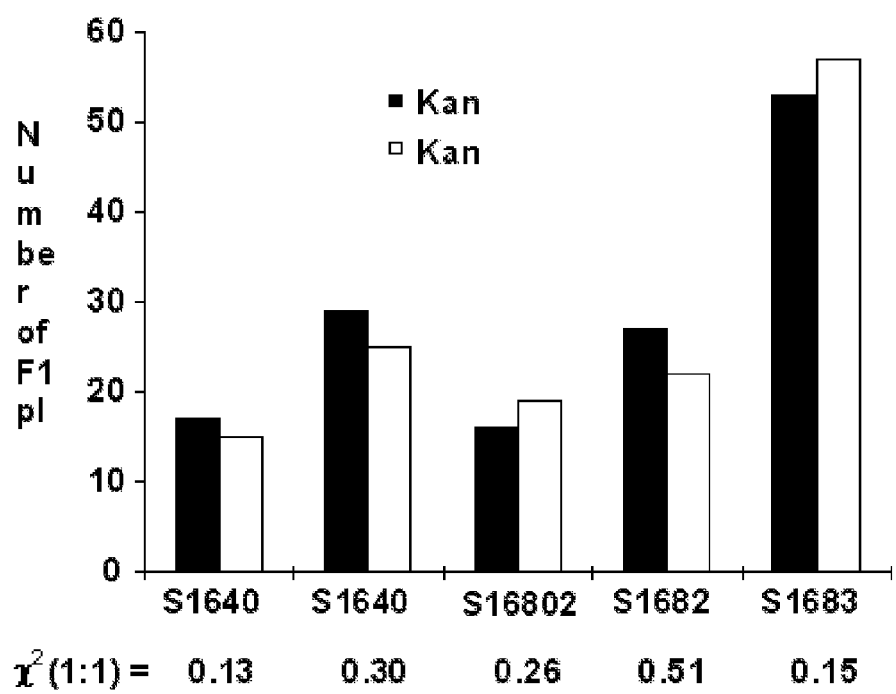
Figure 6:
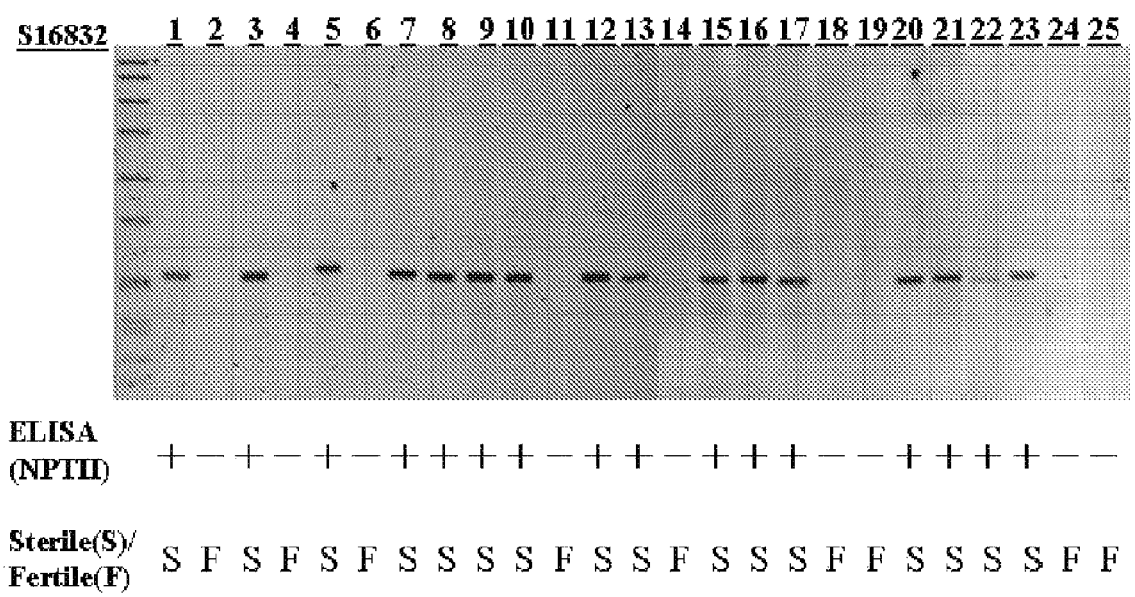
FIG. 6 depicts the male sterile phenotype segregated with the transgene in F1 plants. Twenty-five F1 plants (S16832) were grown to maturity. The transgenic segregants identified by genomic DNA analysis and NPTII ELISA coincide with the male sterile phenotype.

Detection of a single copy of the transgene by DNA gel-blot analysis (FIG. 2A) in these five lines correlated with a 1:1 F1 segregation ratio of the selectable marker (FIG. 2B). These results also indicate that the female gamete development is normal in the transgenic plants. Most of these F1 plants were grown to full maturity and the male sterile phenotype was inherited by plants containing the transgene (FIG. 6). Table 1 details normal transgene transmission from the females of male sterile transgenic plants.

TABLE 1

| Line | Harbored Constructr[a] | (NPTII$^+$/NPII$^-$)[b] | X$^2$(1:1) |
|---|---|---|---|
| S16400 | pMON51827 | 15/17 | 0.13 |
| S16409 | pMON51827 | 25/29 | 0.30 |
| S16802 | pMON51827 | 19/16 | 0.26 |
| S16825 | pMON51826 | 22/27 | 0.51 |
| S16832 | pMON51826 | 57/53 | 0.15 |

[a]CKX1 was driven by pZmg13 (pMON51826) or pZtap (pMON51827) promoter.
[b]The presence or absence of the transgene in the F1 plants was determined by both the antibiotic resistance and the NPTII ELISA from leaf protein extracts. NPTII$^+$, NPTII-positive; NPTII$^-$, NPTII-negative.

Example 4

Western Blots

Figure 3A:
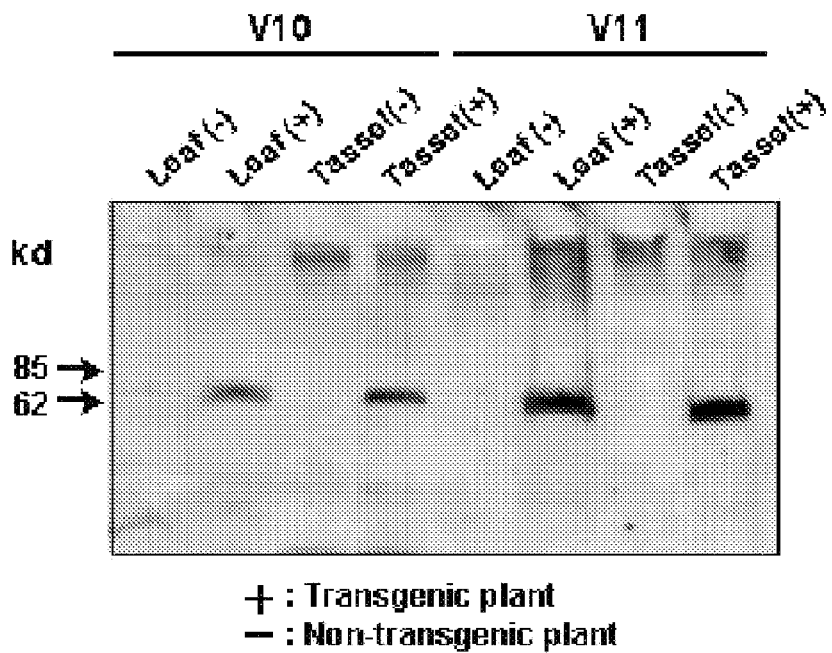
FIGS. 3A-3B detail expression analysis of CKX1 in transgenic plants. (A) The 70 kD CKX1 protein band appeared on the lanes containing transgenic leaves (youngest) and tassels at two stages (V10, V11) in the western blot. Sixty mg of leaf total protein and 20 mg of tassel total protein were loaded on the gel. (B) RT-PCR was performed on the total RNA isolated from leaves and tassels of transgenic and wild type plants. G3PDH was used as a positive cDNA control. CKX1mRNA was detected in the tassels as well as the young leaves (V11 stage) of transgenic plants. CKX1 mRNA was also present in the young leaves at the V8 stage. However, CKX1 transcripts were not detected in the mature leaves. The "no RT" controls consisted of a duplicated set of samples in which reverse transcriptase was not added in the cDNA synthesis step.

In addition to male sterility, the transgenic plants produced from both vectors also exhibited other phenotypic abnormalities. Since cytokinins are known to be involved in many processes of plant growth and development, it was speculated that the observed effects were due to expression of the recombinant construct in non-reproductive tissues despite the presence of male-specific promoters. To test this, protein samples were obtained from transgenic leaves (youngest) and tassels at two stages of development (V10 and V11). Protein samples were prepared in an extraction buffer containing 1× PBS, 1 protein inhibitor cocktail tablet/20ml (Roche Molecular Biochemicals, Indianapolis, Ind.), and 0.05% Tween 20 (v/v), and quantified by Bio-Rad Protein Assay (Hercules, Calif.). Twenty or 60 mg of total protein were separated on a 10-20% Ready Gel and blotted to a 0.2 mm PVDF membrane following the manufacturer's protocol (Bio-Rad). The blot was probed with rabbit anti-CKX1 polyclonal antibody (Bilyeu et al., Plant Physiol., 125:378-386, 2001) at a dilution of 1:10,000, and then incubated with horseradish peroxidase-labeled anti-rabbit antibody at a 1:5,000 dilution. The immunocomplexes were visualized by enhanced chemiluminescence (ECL) according to the instructions of the manufacturer (Amersham Pharmacia, Piscataway, N.J.). The results are shown in FIG. 3A. As shown in the figure, the presence of the CKX1 protein was detected in the leaves and tassels of transgenic plants at both the V10 and V11 stages.

Example 5

RT-PCR

To determine whether the presence of the CKX1 protein in transgenic leaves was due to leaky expression of the male-specific promoters or secretion of the CKX1 protein from male-specific tissues, RNA analysis was performed on the F1 transgenic plants of line S16832. CKX1 transcripts were not detected by total RNA blot analysis, so reverse transcriptase-polymerase chain reaction (RT-PCR) was used. Total RNA was isolated at various stages from leaves and tassels of corn plants by using TRIzol Reagent (Life Technologies, Gaithersburg, Md.) followed by first strand cDNA synthesis (SuperScript™ Preamplication System, Life Technologies) with 2 mg of RNA each in a 20 ml reaction. One ml of the resulting cDNA mix was used in a 30 ml PCR solution containing 1× Reaction Buffer, 15 mM MgCl$_2$, 0.2 mM dNTPs, 6% (v/v) DMSO, 0.2 mM of each primer, and 0.5 unit of Taq DNA Polymerase. The reaction was amplified for 30 cycles. Each cycle consisted of denaturation at 92° C. for 1 min, annealing at 55° C. for 1 min, and extension at 72° C. for 1 min, after an initial denaturation for 2 min. Immediately following the last cycle, the samples were left at 72° C. for 5 min to complete extension. The gene encoding glyceraldehyde-3-phosphate dehydrogenase (G3PDH) (Russell et al., *Plant Cell*, 1:793-803, 1989) was used as a positive control. The sequences of the primers used to amplify NPTII, G3PDH, and CKX1 and predicted product sizes are listed in Table 2. All chemicals and enzymes were from Sigma (St. Louis, Mo.) unless otherwise noted.

TABLE 2

| GENE | PRIMERS | SEQ ID NO. | PRODUCT SIZE (bp) |
|---|---|---|---|
| NPTII | 5'-CGCTTGGGTGGAGAGGCTATTC-3' | 2 | 741 |
|  | 5'-GAAGGCGATAGAAGGCGATGCG-3' | 3 |  |
| G3PDH | 5'-CCCCATGTTCGTTGTTG-3' | 4 | 576 |
|  | 5'-TATCCCCACTCGTTGTCGTACC-3' | 5 |  |
| CKX1 | 5'-CGGCACGCTGTCCAACGC-3' | 6 | 362 |
|  | 5'-GGCTCTGGTTCACGAACACC-3' | 7 |  |

Figure 3B:
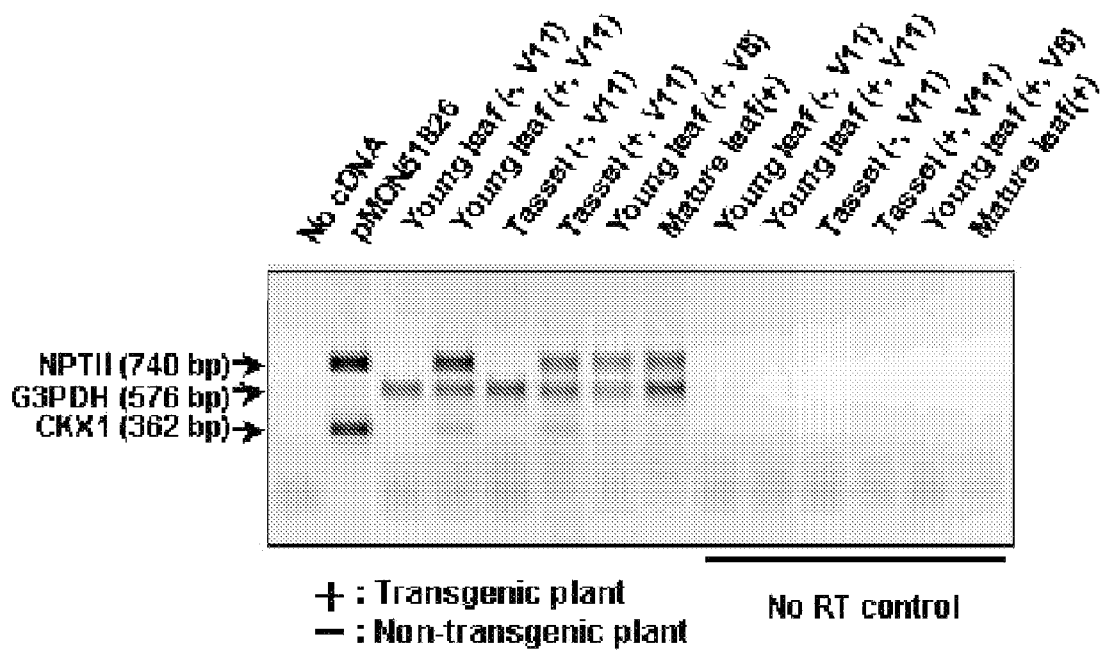

As shown in FIG. 3B, in addition to tassels, the CKX1 mRNA was detected in the young leaves of transgenic plants at V11 stage, where the CKX1 protein accumulated. The CKX1 mRNA was also present in the young leaves at V8, a stage prior to tassel development in transgenic plants. However, unlike neomycin phosphotransferase type II (NPTII) which was driven by a constitutive promoter, enhanced CaMV 35S (e35S) (Fang et al., *Plant Cell*, 1:141-150, 1989), the CKX1 transcripts were not detectable in the mature leaves. The detection of CKX1 expression in non-male tissues by RT-PCR was not due to contamination by genomic DNA, since the negative controls that lack reverse transcriptase were absent of any visible PCR products.

Example 6

Fertility Restoration

Two commercially registered chemicals were tested in fertility restoration experiments. Kinetin is a synthetic cytokinin that is not oxidized by CKX1 and TDZ is a known cytokinin oxidase inhibitor. The F1 seeds from the crosses between wild-type plants and several male-sterile R0 events were planted. NPTII ELISA positive plants were identified as the male-sterile transgenic plants among F1 segregating populations by enzyme-linked immunosorbent assays (ELISA, Example 3) performed on leaf samples collected at the seedling stage of all plants. Identified plants were treated at the V4, V7 and V10 stages. The application rates for each plant were 0, 10, 20, 30, and 100 mg of kinetin with or without 3 mg of TDZ in the presence of 0.25% of Sylgard 309 surfactant (Willbur-Ellis, Fresno, Calif.). One to three plants were tested at a particular rate combination.

Figure 4A:
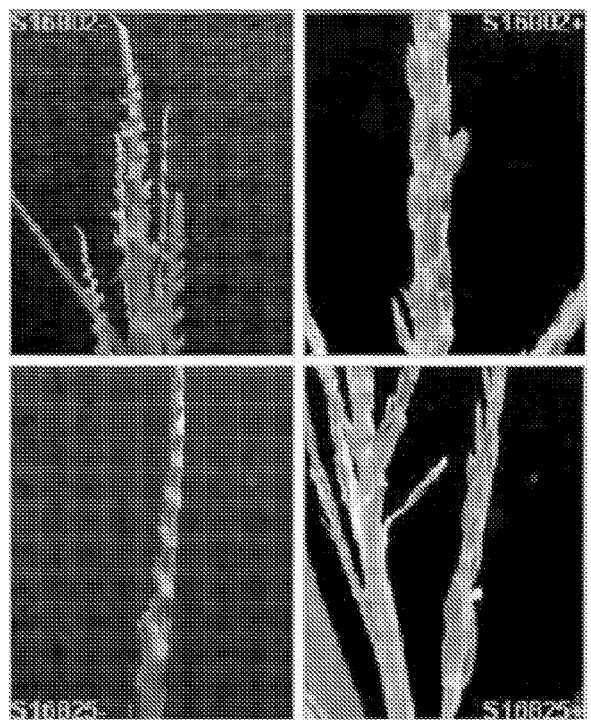
FIGS. 4A-4B delineate improved male organ development of F1 transgenic plants treated with kinetin and TDZ. (A) F1 transgenic plants sprayed with a mixture of kinetin and TDZ (+) or surfactant alone (−). From examples shown as lines S16802 and S16825, advanced floral development was visible on chemically treated plants whereas plants treated with surfactant only were devoid of floral development. (B) Although florets appeared to develop on the transgenic plants after kinetin and TDZ applications, the overall pollen production was insufficient for pollination. Pollen viability stains were then performed using Alexander's solution (Alexander, *Stain Technol.*, 44:117-122, 1969). The chemically restored florets produced viable (purple and symmetrical in shape) pollen (panel I) similar to wild type. Some of the transgenic plants failed to rescue completely resulting in non-viable (blue and asymmetrical in shape) pollen (panel II).
Figure 4B:
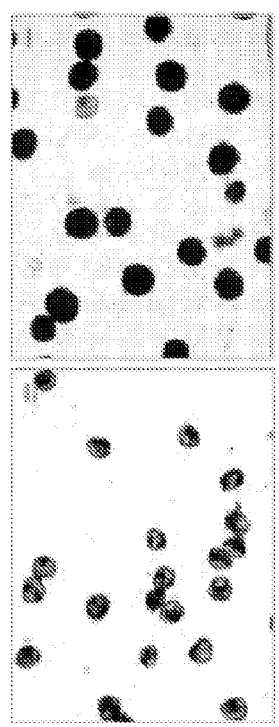

It had previously been shown that these lines had a single transgene insert and that the NTPII ELISA positive phenotype cosegregated with the male sterile phenotype. The NPTII ELISA tests were thus used to select male sterile F1 transgenic plants for chemical treatments. In several instances, as shown in FIG. 4A, the tassels of chemically treated transgenic plants were more developed than controls treated with surfactant only. These chemical application conditions were not sufficient to produce fully fertile plants. The degree of floral development restoration varied and was limited to older tissues of the tassel. In these treated transgenic plants, the earlier flowers produced viable pollen (FIG. 4B, panel I), but the later flowers did not (FIG. 4B, panel II) even though filaments and anthers had developed. Table 3 details tassel fertility rating of the restoration study.

TABLE 3

| Line | TDZ and kinetin applications at V4 + V7 + V10 | | | TDZ and kinetin applications at V7 | |
|---|---|---|---|---|---|
|  | 0, 0[a] | 0, 20 | 3, 20 | 0, 100 | 3, 100 |
| 16802 | 0 | 0 | xx | 0 | x |
| 16825 | 0 | 0 | xx | 0 | x |
| 16832 | 0 | 0 | xx | 0 | 0 |
| 16400 | 0 | 0 | 0 | 0 | x |
| 16409 | 0 | 0 | 0 | 0 | x |

[a] "#, #" indicate mg/plant of TDZ and kinetin in each treatment.

Two to three transgenic F1 plants were used in each treatment group. Plants were either treated repeatedly in three different rates at three V4, V7 and V10 developmental stages or once in a higher rate at V7 developmental stage. Rates are indicated by mg/plant of TDZ and kinetin, respectively, in the presence of 0.25% of Sylgard 309 surfactant. The fertility rating was based on the visual observation. 0, No or very little floral development; x, Advanced floral development observed in some areas of tassels; xx, Increased areas of advanced floral development and anthersis observed in some flowers.

The observation of the aborted pollen in the later flowers supports previous evidence of the requirement of cytokinins in pollen development. Also, on the same tassels that the restored flowers were observed, sectors that lacked floral development remained.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed:

1. A method for producing a plant characterized by reversible male-sterility, the method comprising:
   (a) transforming a plant cell with a first nucleic acid construct containing a polynucleotide encoding a cytokinin oxidase;
   (b) transforming the plant cell with a second nucleic acid construct comprising an inducible promoter and a transcription termination sequence both operably linked to a polynucleotide encoding at least one cytokinin biosynthesis enzyme;
   (c) regenerating a plant from the plant cell wherein expression of the cytokinin oxidase inhibits pollen formation or male organ development in the plant; and
   (d) restoring male-fertility by restoring normal cytokinin levels in the plant.

2. The method of claim 1 wherein the first construct further comprises a regulatory sequence and a transcription termination sequence both operably linked to the polynucleotide encoding the cytokinin oxidase.

3. The method of claim 2 wherein the regulatory sequence comprises a promoter.

4. The method of claim 3 wherein the promoter is selected from the group consisting of constitutive, inducible, environmentally-regulated, developmentally-regulated, organelle-specific, cell-specific, tissue-specific, male specific, anther-specific, pollen-specific, stamen-specific, tapetum-specific promoters and any combination thereof.

5. The method of claim 3 wherein the promoter is a pollen-specific promoter.

6. The method of claim 3 wherein the promoter is an anther-specific promoter.

7. The method of claim 1 further comprising sexually crossing the plant comprising the polynucleotide encoding a cytokinin oxidase with a plant of the same variety comprising a nucleic acid construct containing an inducible promoter and a transcription termination sequence both operably linked to a polynucleotide encoding at least one cytokinin biosynthesis enzyme.

8. The method of claim 1 wherein male-fertility is restored by expression of the polynucleotide encoding at least one cytokinin biosynthesis enzyme.

9. The method of claim 1 further comprising selfing the plant to produce a plant homozygous for the polynucleotide encoding a cytokinin oxidase.

10. A seed from a plant produced by the method of claim 1, wherein said seed comprises the first nucleic acid construct containing a polynucleotide encoding a cytokinin oxidase and the second nucleic acid construct containing a polynucleotide encoding at least one cytokinin biosynthesis enzyme.

11. A uniform population of plants produced by the method of claim 1.

12. A method of producing a hybrid plant comprising sexually crossing a plant produced by the method of claim 1 with a plant of a different variety.

13. A hybrid plant produced by the method of claim 12, wherein said plant comprises the first nucleic acid construct containing a polynucleotide encoding a cytokinin oxidase and the second nucleic acid construct containing a polynucleotide encoding at least one cytokinin biosynthesis enzyme.

14. A seed produced from the plant of claim 13, wherein said seed comprises the first nucleic acid construct containing a polynucleotide encoding a cytokinin oxidase and the second nucleic acid construct containing a polynucleotide encoding at least one cytokinin biosynthesis enzyme.

15. The method of claim 1 wherein the plant is a monocot.

16. The method of claim 15 wherein the monocot is *Zea mays*.

17. The method of claim 1 wherein the cytokinin oxidase comprises cytokinin oxidase 1.

18. The method of claim 1 wherein the polynucleotide encoding cytokinin oxidase is selected from the group consisting of:
   (a) a polynucleotide comprising SEQ ID NO: 1 or the full-length complement thereof;
   (b) a polynucleotide that has at least 90% sequence identity with the polynucleotide of (a);
   (c) a polynucleotide that hybridizes to the polynucleotide of (a) under conditions of 5×SSC, 50% formamide and 42° C., and which encodes a protein having the same biological function;
   (d) a polynucleotide encoding the same amino acid sequence as (a), but which exhibits regular degeneracy in accordance with the degeneracy of the genetic code;
   (e) a polynucleotide encoding the same amino acid sequence as (b), but which exhibits regular degeneracy in accordance with the degeneracy of the genetic code; and
   (f) a polynucleotide encoding the same amino acid sequence as (c), but which exhibits regular degeneracy in accordance with the degeneracy of the genetic code.

* * * * *

SEQUENCE LISTING

<160> NUMBER OF SEQ ID NOS: 24

<210> SEQ ID NO 1

-continued

```
<211> LENGTH: 6732
<212> TYPE: DNA
<213> ORGANISM: Zea mays
<220> FEATURE:
<221> NAME/KEY: misc_feature
<222> LOCATION: (5696)..(5696)
<223> OTHER INFORMATION: n = any nucleotide

<400> SEQUENCE: 1
ctcgagactc cgacgagagg aggctgcgca tgcttgagtc atatcttgga aaaaaaaact      60
gtaacttaaa gtatgatcta tatatggatt atttggatgg gatgtcattt tcgtatcacc    120
aaccaaaatt acagtttggt cgtgcgtaga aattctacct actagctgaa caacggctg     180
ctatgtataa ctactggtac tggaaagaat attagtcatt gactcaaaat tagaatgcat    240
gtgtaagtca tgcgtgctaa tttgttctat cagcattcgg cgaattccga agtccgtacg    300
tgttgttcgt ggaggagagg aaaacatcag aaatgacaaa actagacggt gtgtgcttct    360
acactgaatt cctcaacatt tgttttactt ttactagaga atggcatcaa atggaaaacc    420
gctggaaaaa aaacaacaaa acaattggac cccaaatatg tatacagacg ctagctatag    480
ccagccacac tgaagttgac atgcggcagc tagctagcca ccttctctga aacactaaca    540
tttgtacctt ggtcgtgtaa gtgtagtagt aacgtatgtt gacgcgactt accgaacaaa    600
aatataattg tcccaatcaa gctagggacg attgtttgtt tccaaaatgt tgccatttgc    660
ttaatcaatc ctatattaat tcatggctgt taaggtgaga taaagcgaca agaaatctat    720
atatatgtat ataagatccc gaaggctagc gacatttttg atagcaaaat atgagaagtt    780
tggcagattg ttctggtagc aaatcaaata atatggccag aataatcgtg gctagcttga    840
ttaaaccttc atcagcttgg tgtattttgg aagtcgacca accagctggg ggtcgtcgta    900
cgtagtacca aaattacagc ctgctttcct tcgtcctgta cgtaatgcag tacagctgtc    960
tagtagagac cattttgagg aggcacacac acattaagtg ataacataaa agacggcctg   1020
attttatttc ataaccaaac gatatggtca acacacacct atagctacca aatttgtaca   1080
actatttagt gcgaaaacta tttcattctc aagaattgat cgcttatatt tattattaca   1140
gcttttaaa tgtataaata cgctatattg catggcaaca gggggtaata attaggcagg    1200
actatatata taatagtttt ttcttcttct gtaaattctt gggaggatgg taaagttggt   1260
aactaggcac cttacttgcg cgcatatttt tctgtggtca aacagaataa aactagacgg   1320
gatgcagaat attttttttcc ttggaaagca gctcatcttt tgttcgagt aattgaagaa    1380
gtatgtaatc gcactacacc tacacctata tatatacggg gtgcaatcac ctagttacca   1440
aacactcaca cataacgtat agctctctct ctctcccgtg aacgacgacg tcgctaatgg   1500
cggtggttta ttacctgctg ctggccgggc tgatcgcctg ctctcatgca ctagcggcag   1560
gcacgcctgc gctcggagac gatcgcggcc gtccctggcc agcctccctc gccgcgctgg   1620
ccttggacgg caagctccgg accgacagca acgcgacggc ggcggcctcg acggacttcg   1680
gcaacatcac gtcggcgctc ccggcggcgg tcctgtaccc gtcgtccacg ggcgacctgg   1740
tggcgctgct gagcgcggcc aactccaccc cggggtggcc ctacaccatc gcgttccgcg   1800
gccgcggcca ctccctcatg ggccaggcct tcgcccccgg cggcgtcgtc gtcaacatgg   1860
cgtccctggg cgacgccgcc gcgccgcgc gcatcaacgt gtccgcggac ggccgctacg   1920
tggacgccgg cggcgagcag gtgtggatcg acgtgttgcg cgcgtcgctg gcgcgcggcg   1980
tggcgccgcg ctcctggaac gactacctct acctcaccgt cggcggcacg ctgtccaacg   2040
caggcatcag cggccaggcg ttccgccacg gcccacagat atctaacgtg ctggagatgg   2100
```

```
acgttatcac cggtacgtgt gcacctacta ctacttttc cctcccttgc acaagtgcac    2160
aaccacacca cagcaagcga gcaaaagctt gttttttttt tacgtgccag tacacctgca    2220
tcgacttctg ttgcttgcca cggggcaaca ccgtgttcaa tcagccggat tgaaattcgt    2280
tacctacatt gcgaatcata tatttatttt tttagtatta ttagtggtgc atggtggtta    2340
atgtccgcgc tgcaccggcc ggccgcccgc ccggccggcg aggggcggcg acgtctttaa    2400
taactagtca taaatcagca tgcatgctgg ctctcgcagc tggtgcgttg acattgtgcc    2460
tttgttcgtt tcggctaata gaattatatt gctggggtgt tgactttgtg gtgatcgaac    2520
gcaggccatg gggagatggt gacgtgctcc aagcagctga acgcggacct gttcgacgcc    2580
gtcctgggcg ggctggggca gttcggagtg atcacccggg cccggatcgc ggtggagccg    2640
gcgccggcgc gggcgcggtg ggtgcggttc gtgtacaccg acttcgcggc gttcagcgcc    2700
gaccaggagc ggctgaccgc cccgcggccc ggcggcggcg gcgcgtcgtt cggcccgatg    2760
agctacgtgg aagggtcggt gttcgtgaac cagagcctgg cgaccgacct ggcgaacacg    2820
gggttcttca ccgacgccga cgtcgcccgg atcgtcgcgc tcgccgggga gcggaacgcc    2880
accaccgtgt acagcatcga ggccacgctc aactacgaca acgccacggc ggcggcggcg    2940
gcggtggacc aggagctcgc gtccgtgctg ggcacgctga gctacgtgga ggggttcgcg    3000
ttccagcgcg acgtggccta cgcggcgttc cttgaccggg tgcacggcga ggaggtggcg    3060
ctcaacaagc tggggctgtg gcgggtgccg cacccgtggc tcaacatgtt cgtgccgcgc    3120
tcgcgcatcg ccgacttcga ccgcggcgtg ttcaagggca tcctgcaggg caccgacatc    3180
gtcggcccgc tcatcgtcta cccccctcaac aaatccatgt acgtgttgaa tcgatcggct    3240
agctagctag ctaggcacgc cccggccggc ctctgacgac tcgaccggtc tttctggggt    3300
ttggtttttc aggtgggacg acggcatgtc ggcggcgacg ccgtctgagg acgtgttcta    3360
cgcggtgtcg ctgctcttct cgtcggtggc gcccaacgac ctggcgaggc tgcaggagca    3420
gaacaggagg atcctgcgct tctgcgacct cgccgggatc cagtacaaga cctacctggc    3480
gcggcacacg gaccgcagtg actgggtccg ccacttcggc gccgccaagt ggaatcgctt    3540
cgtggagatg aagaacaagt acgaccccaa gaggctgctc tcccccggcc aggacatctt    3600
caactgatga tgatagccca tgcatgtttt agttcttgg acaataatg tgaataattc    3660 ccagctagcg gctattaatt aatctgtata tagattgatc actgcactga tgtatgtcaa    3720
ggtcattatt tacgttatgg taaaaaaaaa agtaccctcg tcgtatattc tcgtttcatc    3780
tgcccaaccc ccagagtttt aaaaatgcac gttgagagca aaatttccac accgtttatc    3840
catgtagtag attgggtgta tattgaatcc gtataaatat atagcaagac aaaatttatt    3900
gcaatctgat cccgtacacc ataattcaca tgaaattaga ataaccgaac aaaaggactt    3960
gttagtatgg gttgccgttg cacttttttt gtgtgcctat ttaggtatga tatagttctg    4020
ccaaacatta tttgacagtc aaatacatcc ctgtcgtcct aataggcgtc caaaatcaaa    4080
cgtgtgttta gccagccccc atccaaacac gcccatatcc ctattttctt tgccttccct    4140
tttaattttt gtttttttt cctcttcaaa taataactgg tcctcaacta gtcacttaaa    4200
aaaaaggaag agtgtgaagg agaaggaaaa agacaccgtc acttgtgaaa caaattaaaa    4260
agtttcttgg atcgaggcgc gtgatactct ctcaccctgc acgttttgct tcgatctccg    4320
acggcaccgt ccgtcatttt ctacaaaata cgaaaccttg ttccgtgctt gttgatcaga    4380
cagctgacgt cgacaagttc aggtaaaggg tcatttgcgc gaccagcagg tcggctggtg    4440
ttgaactgat tcttttaaac ttaatgataa ccagtagagt agacaccatt gattctttta    4500
```

```
aactttaacc gctagtctta ttcaaaatat ttatttaaaa tgtataatttt taaatcaagc    4560
cagactacat caagtgataa aacaaatcat aataaaatta atgataactt attattgttt    4620
tgaataagac gaacgatcaa agttttaaaa ataaacggtg tcatatacgg agggagtact    4680
agcttagtac cccggttgac cagaggtgcg gtgtgcctta attcgatcgt tttctcttgt    4740
ttcctcagcg ttcaccacat gcactgcact tgcaagccgt acacgttgac tagtggggca    4800
atgctagctt ggtgaggttt tttgattgat tcccagcttt tagacgaggt cactccacaa    4860
aaaaagctaa gcaacggtgc tgacctgaat aaataaaggt ggtcgtagat tattggttat    4920
agccgtcgtc acaggtcaca cacacgcaac aagcctatag caggattaca ccgattatca    4980
tcgggaaata gaaaaaaggg aaatgaacga agtaaccagg agacagacga cgagaaagta    5040
ttgtctatcc ttaagacccc cttgagcaag ctacacggta aattaggctc ccatcggacg    5100
tcatttctgg acacgtacgc tattgtgatt tgtaagggtg tttggtttct aaatactaat    5160
ttttagccac tctttattat tatattctag tcactaaatt atcaaatacg aaaattaaaa    5220
tagatttta attttaagta ttttgtaatt tatgtactag aatggaataa aatggtgtga    5280
ttaaaaatta gtccctaaaa atcaaatgtc attcccccct tattagaaga cctcttgagc    5340
aagctaagct gcacgtatta ttaggcctca acatgcctat gtgtgtataa caggacaacc    5400
aggccccca aacttcagtt gtacgtatgt gtaacatgta ctgtgaggac aatcgatctc    5460
aaacgtcagc tgtaggtacg tatgaatgta tatatgtgta tttactcctc ctgtttaaa    5520
tcagttgtcg cgatggtatt tatgtccatc aaagtttgtt agagtagact agcttttttag    5580
aaaatgttag tcacatttat atcctcaaat aaacttactt ataaaaataa attcaatgat    5640
ctatttaata atataacgat actaatcatg taatatgaat ataaatattt tcttgnacat    5700
atttgatgaa gtttaaaata gttagttttt aaaaaaataa aaacaccgac tattttaaaa    5760
tagatagagt acatatacaa gaaaatgaga aattattact aatgtttaca acgtataata    5820
aataatatat aaattatgaa atatatttt ataataaatc tgtttagaga agataatatt    5880
ttctacgact ccttgttcaa atctagaatg acattatttt tgggacggag gcagttcgta    5940
ctacgtacgt aacatgtatt cctaacacgg acaatcaaaa catgggaact tcactccatt    6000
tgtaaagccg ggggcggaat cggtggamgt gtttgtttct tggcgcacgg tgaytcgatg    6060
aggattcgtg caaaccttaa maggcttggt catctgtctg cattcaytcc acacggccat    6120
acgcacgtgt ttttctggat gggcatgaac acggacacgg cacgcatctc aagtcagggc    6180
agttaaaggg agacgcgtgg gaacatgata ccagggttgc atcttcacaa aattggccgt    6240
atgtgctaca tcatcagggg gagcagccat aatttacatg gaaacgaata caatgatgga    6300
gcacgtcagt ggctattatt cttcaatgag gctacagcta cactatttga tgcacatcag    6360
ctactgcctc ctagtccttg gcgcccacc tccacacttt cagctcgccg gagcagtctc    6420
cggtgaagag cagcccacca gccgcaagct cgatggtcct aacttccttc gtggacaaca    6480
gtgttccaat cccgtcgaac ctgaaagatg gtaaccaggc aaatgcagag ctccttcag    6540
taaggaacca ctgagcgagc ggtttgtcta tctgatgatg aaactgataa aaaaaatta    6600
tgcactcacg atggcaagtc gagcaagcgg acgcgattgc tgttgtggag ggagcacaag    6660
agaactggcg tcttcccaac tcggtgcatg ccgaagagtg tgcgcaaacc ctgcaacata    6720
atcggaaagc tt                                                        6732

<210> SEQ ID NO 2
<211> LENGTH: 22
<212> TYPE: DNA
```

```
<213> ORGANISM: Artificial sequence
<220> FEATURE:
<223> OTHER INFORMATION: Primer

<400> SEQUENCE: 2
cgcttgggtg gagaggctat tc                                              22

<210> SEQ ID NO 3
<211> LENGTH: 22
<212> TYPE: DNA
<213> ORGANISM: Artificial sequence
<220> FEATURE:
<223> OTHER INFORMATION: Primer

<400> SEQUENCE: 3
gaaggcgata gaaggcgatg cg                                              22

<210> SEQ ID NO 4
<211> LENGTH: 17
<212> TYPE: DNA
<213> ORGANISM: Artificial sequence
<220> FEATURE:
<223> OTHER INFORMATION: Primer

<400> SEQUENCE: 4
ccccatgttc gttgttg                                                    17

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
tatccccact cgttgtcgta cc                                              22

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
cggcacgctg tccaacgc                                                   18

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
ggctctggtt cacgaacacc                                                 20

<210> SEQ ID NO 8
<211> LENGTH: 1506
<212> TYPE: DNA
<213> ORGANISM: Arabidopsis thaliana

<400> SEQUENCE: 8
atggctaatc ttcgtttaat gatcacttta atcacggttt taatgatcac caaatcatca     60
aacggtatta aaattgattt acctaaatcc cttaacctca ccctctctac cgatccttcc    120
```

|  |  |  |  |
|---|---|---|---|
| atcatctccg cagcctctca tgacttcgga aacataacca ccgtgacccc cggcggcgta | 180 |
| atctgcccct cctccaccgc tgatatctct cgtctcctcc aatacgccgc aaacggaaaa | 240 |
| agtacattcc aagtagcggc tcgtggccaa ggccactcct taaacggcca agcctcggtc | 300 |
| tccggcggag taatcgtcaa catgacgtgt atcactgacg tggtggtttc aaaagacaag | 360 |
| aagtacgctg acgtggcggc cgggacgtta tgggtggatg tgcttaagaa gacggcggag | 420 |
| aaaggggtgt cgccggtttc ttggacggat tatttgcata taaccgtccg aggaacgttg | 480 |
| tcgaatggtg gaattggtgg tcaagtgttt cgaaacggtc tcttgttag taacgtcctt | 540 |
| gaattggacg ttattactgg gaaaggtgaa atgttgacat gctcgcgaca gctaaaccca | 600 |
| gaattgttct atggagtgtt aggaggtttg ggtcaatttg gaattataac gagagccaga | 660 |
| attgttttgg accatgcacc taaacgggcc aaatggtttc ggatgctcta cagtgatttc | 720 |
| acaactttta caaaggacca agaacgtttg atatcaatgg caaacgatat tggagtcgac | 780 |
| tatttagaag gtcaaatatt tctatcaaac ggtgtcgttg acacctcttt tttcccacct | 840 |
| tcagatcaat ctaaagtcgc tgatctagtc aagcaacacg gtatcatcta tgttcttgaa | 900 |
| gtagccaagt attatgatga tcccaatctc cccatcatca gcaaggttat tgacacatta | 960 |
| acgaaaacat taagttactt gcccgggttc atatcaatgc acgacgtggc ctacttcgat | 1020 |
| ttcttgaacc gtgtacatgt cgaagaaaat aaactcagat ctttgggatt atgggaactt | 1080 |
| cctcatcctt ggcttaacct ctacgttcct aaatctcgga ttctcgattt tcataacggt | 1140 |
| gttgtcaaag acattcttct taagcaaaaa tcagcttcgg gactcgctct tctctatcca | 1200 |
| acaaaccgga ataaatggga caatcgtatg tcggcgatga taccagagat cgatgaagat | 1260 |
| gttatatata ttatcggact actacaatcc gctaccccaa aggatcttcc agaagtggag | 1320 |
| agcgttaacg agaagataat taggttttgc aaggattcag gtattaagat taagcaatat | 1380 |
| ctaatgcatt atactagtaa agaagattgg attgagcatt ttggatcaaa atgggatgat | 1440 |
| ttttcgaaga ggaaagatct atttgatccc aagaaactgt tatctccagg gcaagacatc | 1500 |
| ttttga | 1506 |

<210> SEQ ID NO 9
<211> LENGTH: 1572
<212> TYPE: DNA
<213> ORGANISM: Arabidopsis thaliana

<400> SEQUENCE: 9

|  |  |  |  |
|---|---|---|---|
| atggcgagtt ataatcttcg ttcacaagtt cgtcttatag caataacaat agtaatcatc | 60 |
| attactctct caactccgat cacaaccaac acatcaccac aaccatggaa tatccttttca | 120 |
| cacaacgaat tcgccggaaa actcacctcc tcctcctcct ccgtcgaatc agccgccaca | 180 |
| gatttcggcc acgtcaccaa aatcttccct tccgccgtct taatcccttc ctccgttgaa | 240 |
| gacatcacag atctcataaa actctctttt gactctcaac tgtctttttcc tttagccgct | 300 |
| cgtggtcacg gacacagcca ccgtggccaa gcctcggcta agacggagt tgtggtcaac | 360 |
| atgcggtcca tggtaaaccg ggatcgaggt atcaaggtgt ctaggacctg tttatatgtt | 420 |
| gacgtggacg ctgcgtggct atggattgag tgttgaata aaactttgga gttagggtta | 480 |
| acgccggttt cttggacgga ttatttgtat ttaacagtcg gtgggacgtt atcaaacggc | 540 |
| ggaattagtg gacaaacgtt tcggtacggt ccacagatca ctaatgttct agagatggat | 600 |
| gttattactg gaaaaggaga gattgcaact tgttccaagg acatgaactc ggatcttttc | 660 |
| ttcgcggtgt taggaggttt gggtcaattc ggcattataa caagagccag aattaaactt | 720 |

```
gaagtagctc cgaaaagggc caagtggtta aggtttctat acatagattt ctccgaattc    780
acaagagatc aagaacgagt gatatcgaaa acggacggtg tagatttctt agaaggttcc    840
attatggtgg accatggccc accggataac tggagatcca cgtattatcc accgtccgat    900
cacttgagga tcgcctcaat ggtcaaacga catcgtgtca tctactgcct tgaagtcgtc    960
aagtattacg acgaaacttc tcaatacaca gtcaacgagg aaatggagga gttaagcgat   1020
agtttaaacc atgtaagagg gtttatgtac gagaaagatg tgacgtatat ggatttccta   1080
aaccgagttc gaaccggaga gctaaacctg aaatccaaag gccaatggga tgttccacat   1140
ccatggctta atctcttcgt accaaaaact caaatctcca aatttgatga tggtgttttt   1200
aagggtatta tcctaagaaa taacatcact agcggtcctg ttcttgttta tcctatgaat   1260
cgcaacaagt ggaatgatcg gatgtctgcc gctatacccg aggaagatgt attttatgcg   1320
gtagggtttt taagatccgc gggttttgac aattgggagg cttttgatca agaaaacatg   1380
gaaatactga gtttttgtga ggatgctaat atggggggtta tacaatatct tccttatcat   1440
tcatcacaag aaggatgggt tagacatttt ggtccgaggt ggaatatttt cgtagagaga   1500
aaatataaat atgatcccaa aatgatatta tcaccgggac aaaatatatt tcaaaaaata   1560
aactcgagtt ag                                                       1572

<210> SEQ ID NO 10
<211> LENGTH: 1575
<212> TYPE: DNA
<213> ORGANISM: Arabidopsis thaliana

<400> SEQUENCE: 10
atgactaata ctctctgttt aagcctcatc accctaataa cgttttttat aagtttaacc     60
ccaaccttaa tcaaatcaga tgagggcatt gatgttttct acccatatc actcaacctt    120
acggtcctaa ccgatccctt ctccatctct gccgcttctc acgacttcgg taacataacc    180
gacgaaaatc ccggcgccgt cctctgccct tcctccacca cggaggtggc tcgtctcctc    240
cgtttcgcta acggaggatt ctcttacaat aaaggctcaa ccagccccgc gtctactttc    300
aaagtggctg ctcgaggcca aggccactcc ctccgtggcc aagcctctgc acccggaggt    360
gtcgtcgtga acatgacgtg tctcgccatg gcggctaaac cagcggcggt tgttatctcg    420
gcagacggga cttacgctga cgtggctgcc gggacgatgt gggtggatgt tctgaaggcg    480
gcggtggata gaggcgtctc gccggttaca tggacggatt atttgtatct cagcgtcggc    540
gggacgttgt cgaacgctgg aatcggtggt cagacgttta cacggcccc tcagattagt    600
aacgttcatg agcttgacgt tattaccgga aaaggtgaaa tgatgacttg ctctccaaag    660
ttaaaccctg aattgttcta tggagtttta ggaggtttgg gtcaattcgg tattataacg    720
agggccagga ttgcgttgga tcatgcaccc acaagggtga atggtctcg catactctac    780
agtgacttct cggcttttaa aagagaccaa gagcgtttaa tatcaatgac caatgatctc    840
ggagttgact ttttggaagg tcaacttatg atgtcaaatg gcttcgtaga cacctctttc    900
ttcccactct ccgatcaaac aagagtcgca tctcttgtga atgaccaccg gatcatctat    960
gttctcgaag tagccaagta ttatgacaga accacccttc ccattattga ccaggtgatt   1020
gacacgttaa gtagaactct aggtttcgct ccagggttta tgttcgtaca agatgttccg   1080
tatttcgatt tcttgaaccg tgtccgaaac gaagaagata aactcagatc tttaggacta   1140
tgggaagttc ctcatccatg gcttaacatc tttgtcccgg ggtctcgaat ccaagatttt   1200
catgatggtg ttattaatgg ccttcttcta aaccaaacct caacttctgg tgttactctc   1260
```

```
ttctatccca caaaccgaaa caaatggaac aaccgcatgt caacgatgac accggacgaa    1320 gatgttttttt atgtgatcgg attactgcaa tcagctggtg gatctcaaaa ttggcaagaa    1380
cttgaaaatc tcaacgacaa ggttattcag ttttgtgaaa actcgggaat taagattaag    1440
gaatatttga tgcactatac aagaaaagaa gattgggtta acatttttgg accaaaatgg    1500
gatgattttt taagaaagaa aattatgttt gatcccaaaa gactattgtc tccaggacaa    1560
gacatattta attaa                                                    1575

<210> SEQ ID NO 11
<211> LENGTH: 1575
<212> TYPE: DNA
<213> ORGANISM: Arabidopsis thaliana

<400> SEQUENCE: 11
atgatagctt acatagaacc atacttcttg gaaaacgacg ccgaggctgc ctctgccgcc      60
accgccgccg gaaaatctac ggatggtgtt tctgagtcac ttaacatcca aggagaaatc     120
ttatgtggtg gagctgcggc ggatatcgcc gggagagatt ttggcggcat gaactgtgtg     180
aagcctcttg ctgtggtgag accagtggga ccggaagata tcgccggagc ggtgaaagcg     240
gctctgaggt cagataaact aacggtggcg gcgcgtggaa acggccattc tatcaacggt     300
caagccatgg cggaaggagg actcgttgtc gatatgagta ccacggcgga gaatcatttc     360
gaggttggtt atttatccgg cggtgatgcc acggcgtttg ttgatgtctc cggagggca     420 ttatgggaag atgtattgaa acggtgcgtt tcggagtacg gtttggctcc gaggtcttgg     480
actgattatc ttgggttaac ggtgggaggt acgttgtcaa atgccggcgt tagtggtcaa     540
gcgttccgtt acggaccaca gacgtcaaat gtaacggagt tggacgtcgt tacgggaaat     600
ggtgacgtcg ttacttgctc ggagattgag aattcagagc tattcttctc tgttttaggt     660
ggtcttggtc agtttggtat catcaccaga gctagggttt tgctacagcc agctcctgat     720
atggtgagat ggataagagt agtatacacc gagttcgatg agttcactca agacgccgag     780
tggctagtaa gtcagaagaa cgagtcatcg ttcgattacg tggaaggatt cgtgtttgtc     840
aacggtgctg acccggttaa cggatggcca acagttcccc tccacccgga ccacgagttt     900
gacccgaccc gactaccaca atcttgcggg tcggttcttt attgcctcga actcggtctt     960
cactacagag actccgattc caactcaacc attgacaaga gggtggagag attgatcgga    1020
cggctaagat ttaatgaagg attaagattc gaggtagatc tgccgtacgt tgactttta    1080 ctacgagtca acggtcaga agaaatcgcg aaggagaacg gtacgtggga aacgcctcac    1140
ccttggctca acctcttcgt gtcgaagcga gacatcggag atttcaatcg gacggtgttc    1200
aaagaacttg tcaagaacgg agtcaatggt ccaatgcttg tgtacccact cttgcgaagc    1260
aggtgggatg atcggacgtc cgtggttata ccggaagaag gagagatatt ctacattgtg    1320
gcattgcttc ggttcgtgcc gccgtgtgcg aaagtctctt cggtagagaa aatggtagct    1380
caaaaccaag agatcgttca ttggtgtgtc aaaaacggaa ttgattacaa attgtatctt    1440
cctcattaca agtctcaaga ggaatggatt cgccattttg gaaaccgatg gtcgagattt    1500
gttgatagga aagctatgtt tgatcccatg gctatacttt caccgggtca aaagattttc    1560
aataggtctc tttga                                                    1575

<210> SEQ ID NO 12
<211> LENGTH: 1623
<212> TYPE: DNA
<213> ORGANISM: Arabidopsis thaliana
```

```
<400> SEQUENCE: 12
atgaatcgtg aaatgacgtc aagctttctt ctcctgacgt tcgccatatg taaactgatc        60
atagccgtgg gtctaaacgt gggcccagt gagctcctcc gcatcggagc catagatgtc       120
gacggccact tcaccgtcca cccttccgac ttagcctccg tctcctcaga cttcggtatg       180
ctgaagtcac ctgaagagcc attggccgtg cttcatccat catcggccga agacgtggca       240
cgactcgtca gaacagctta cggttcagcc acggcgtttc cggtctcagc ccgaggccac       300
ggccattcca taaacggaca agccgcggcg gggaggaacg gtgtggtggt tgaaatgaac       360
cacggcgtaa ccgggacgcc caagccactc gtccgaccgg atgaaatgta tgtggatgta       420
tggggtggag agttatgggt cgatgtgttg aagaaaacgt tggagcatgg cttagcacca       480
aaatcatgga cggattactt gtatctaacc gttggaggta cactctccaa tgcaggaatc       540
agtggtcaag ctcttcacca tggtcctcaa attagtaacg tccttgagct cgacgttgta       600
actgggaaag gagaggtgat gagatgctca gaagaagaga cacaaggct attccatgga        660
gttcttggtg gattaggtca atttgggatc atcactcgag cacgaatctc tctcgaacca       720
gctccccaaa gggtgagatg gatacgggta ttgtattcga gcttcaaagt gtttacggag       780
gaccaagagt acttaatctc aatgcatggt caattaaagt ttgattacgt ggaaggtttt       840
gtgattgtgg acgaaggact cgtcaacaat tggagatctt ctttcttctc tccacgtaac       900
cccgtcaaga tctcctctgt tagctccaac ggctctgttt tgtattgcct tgagatcacc       960
aagaactacc acgactccga ctccgaaatc gttgatcagg aagttgagat tctgatgaag      1020
aaattgaatt tcataccgac atcggtcttt acaacggatt tacaatatgt ggactttctc      1080
gaccgggtac acaaggccga attgaagctc cggtccaaga atttatggga ggttccacac      1140
ccatggctca acctcttcgt gccaaaatca agaatctctg acttcgataa aggcgttttc      1200
aagggcattt tgggaaataa acaagtggcc ctattcttta ctacccccat gaacaaagac      1260
aaatgggacg agaggagctc agccgtgacg ccggatgagg aagttttcta tctggtggct      1320
ctattgagat cagctttaac ggacggtgaa gagacacaga agctagagta tctgaaagat      1380
cagaaccgtc ggatcttgga gttctgtgaa caagccaaga tcaatgtgaa gcagtatctt      1440
cctcaccacg caacacagga agagtgggtg gctcattttg gggacaagtg ggatcggttc      1500
agaagcttaa aggctgagtt tgatccgcga cacatactcg ctactggtca gagaatcttt      1560
caaaacccat ctttgtcttt gtttcctccg tcgtcgtctt cttcgtcagc ggcttcatgg      1620
tga                                                                    1623

<210> SEQ ID NO 13
<211> LENGTH: 525
<212> TYPE: DNA
<213> ORGANISM: Glycine max

<400> SEQUENCE: 13
aacaacaaag cactctctct tctctcattc tattatcttc tctcatcctc ttattctctc         60
caaaccaaca aaaaaaaaat ggttgctgag aactaccctt ctcccacata cttcatcctc        120
ctgttcataa ccataacacg tttgatctcc acagtgggca aaacctccca atggacgaag        180
gccctgtcgc tgcctccgga actcgcctcc gtctccctcg acgacaccat cttctgcaag        240
ctccgtgacg acccagaggc cctccaggga agggcctcca gggactacgg gaacctcgtc        300
cgcgaggttc ccttggcagt cttccaccca gcctcagcga gcgacatcgc gaggctgatc        360
aagctgtcgt acaacggctc tgtcccttc aagattgcgg cgaggggca agggcactcg         420
```

```
acaaggggcc aggcgatggc acgtgagggg gtggtggtgg acatggcggg gttcagagag    480
agagggaatg gagtgcggat aagggttgtg ggttacgtgg accct                   525
```

\<210\> SEQ ID NO 14
\<211\> LENGTH: 566
\<212\> TYPE: DNA
\<213\> ORGANISM: Glycine max

\<400\> SEQUENCE: 14

```
agtgtctcta aggacccttt gatgggtcac tatgcggatg ttggagggga caactctgg     60 attgatgtgc tacataccac acttaaacat ggacttgcac cagtttcttg gactgattat   120
ttgtacttga ccgtgggagg gacactttcc aatgctggaa tcagtggcca gagcttccgt   180
tatggacctc aaatcagcaa cgttcatgaa atggatgtca tcactggaaa ggagagttc    240 gtaacttgct cttcacagaa gaacttggag ttattccacg cggttcttgg aggcttaggg   300
caatttggag ttatagcaag ggcgagaata gcacttgagc cagccccaa aagggttaag   360 tgggtcagac tactttatag tgactttttt gcttttacca agatcagga acgattaatc   420 tcaatcaatg gaaggaaaca aaagaacgca ttggattttc tggaagggat gctgctaatg   480
aaccaaggcc ccataaataa ttggagatcc tcttcttcc ctctatctga ccatcccaga   540
atatcttctt taataactga acatag                                        566
```

\<210\> SEQ ID NO 15
\<211\> LENGTH: 552
\<212\> TYPE: DNA
\<213\> ORGANISM: Glycine max

\<400\> SEQUENCE: 15

```
tattccacgc ggttcttgga ggcttagggc aatttggagt tatagcaagg gcgagaatag    60
cacttgagcc agcccccaaa agggttaagt gggtcagact actttatagt gacttttttg   120
cttttaccaa agatcaggaa cgattaatct caatcaatgg aaggaaacaa aagaacgcat   180
tggattttct ggaagggatg ctgctaatga accaaggccc cataaataat tggagatcct   240 cttcttccc tctatctgac catcccagaa tatcttcttt aataactgaa catagcatcc   300
tctactgtct tgaagtggct aaatattatg acgaacaaac cgagataaat gtggacaagg   360
aaattcaagt tttgctccaa ggactagcct atatccctgg ttttattat gagaaaaacg   420 tgtcgtacgt tgagttcttg aatagggtcc gaagtggaga gttgaagctt cagtcacaag   480
gactgtggga tgttcctcac ccatggctta atttgtttat accaaaatct caaatcttgg   540 atttaattc aa                                                        552
```

\<210\> SEQ ID NO 16
\<211\> LENGTH: 635
\<212\> TYPE: DNA
\<213\> ORGANISM: Glycine max

\<400\> SEQUENCE: 16

```
agcgttatgg acctcaaatc agcaacgttc atgaaatgga tgtcatcact ggaaaaggag    60
agttcgtaac ttgctcttca cagaagaact tggagttatt ccacgcggtt cttggaggct   120
tagggcaatt tggagttata gcaagggcga gaatagcact tgagccagcc cccaaaggg   180 ttaagtgggt cagactactt tatagtgact ttttgcttt taccaaagat caggaacgat   240
taatctcaat caatggaagg aaacaaaaga acgcattgga ttttctggaa gggatgctgc   300
taatgaacca aggcccata aataattgga gatcctcttt cttccctcta tctgaccatc   360
```

```
ccagaatatc ttctttaata actgaacata gcatcctcta ctgtcttgaa gtggctaaat      420
attatgacga acaaaccgag ataaatgtgg acaatgaaat tcaagttttg ctacaaggac      480
tagcctatat ccctgtgtta tattatgaga aaaacgtgtc atacgttgag ttcttgaata      540
gggtccaaag aggacaggtg gagcttcact cacaaggact gttggatgtt actcactcat      600
ggcttaatat gtatatacca aagtctcgaa tcttg                                 635
```

<210> SEQ ID NO 17
<211> LENGTH: 236
<212> TYPE: DNA
<213> ORGANISM: Glycine max
<220> FEATURE:
<221> NAME/KEY: misc_feature
<222> LOCATION: (218)..(218)
<223> OTHER INFORMATION: n = a, t, c, or g

<400> SEQUENCE: 17

```
acgagcaagg ccccataaat aattggagat cctctttctt ccctctatct gaccatccca       60
gaatagcttc tttaataact gaacatagca tcctctactg tcttgaagtg gctaaatatt      120
atgacgaaca aaccgagtta aatgtggaca aggaaattga agttttgctc caaggactag      180
cctatatccc tggatttaat tatgagaaaa atgtctcnta cgttggagtt cttgat         236
```

<210> SEQ ID NO 18
<211> LENGTH: 582
<212> TYPE: DNA
<213> ORGANISM: Glycine max

<400> SEQUENCE: 18

```
ggaaaaggag agttcgtaac atgctcttca cagaagaact ggagttatt ccacgcggtt        60 cttggaggct tgggacaatt tggagttata gcaagggcga gaattgctct tgagccagca     120
cccaaaaggg ttaagtgggt cagactactt tatagtgact tttctgcttt taccaaagac     180
caggaacgat taatctcaat caatggaagg aaacaaaaga acgcattgga ttttctggaa     240
gggatgctgc taatgaacca aggccccata ataattgga gatcctcttt cttccctcta     300
tctgaccatc ccagaatagc ttctttaata actgaacata gcatcctcta ctgtcttgaa     360
gtggctaaat attatgacga acaaaccgag ttaaatgtgg acaaggaaat tgaagttttg     420
ctccaaggac tagcctatat ccctggattt aattatgaga aaaatgtctc gtacgttgag     480
ttcttgaata gggtccgaag tggagagttg aaacttcagt cacaaggact gtgggaagtt     540
cctcacccgt ggcttaattt gtttatacca aaatctcaaa tc                        582
```

<210> SEQ ID NO 19
<211> LENGTH: 414
<212> TYPE: DNA
<213> ORGANISM: Glycine max

<400> SEQUENCE: 19

```
gctcgctctt cactatcgta acgcggatca tccttctcgt gtcgatacgg atgtggatgg       60
attgcttgga cggctacgat tcattcaggg tctgaagttc caggtggacg tgacatacat     120
ggagttcttg ctgcgtgtaa agcgtgtgga ggagcacgcg aaaggcaacg gaacctggga     180
tgcacctcac ccttggctca atctgttcgt gtccaagtcc cacatcgttg attttgatcg     240
tgaggtgttc aagaagattc tcaaggacgg agtcgatgga cccatttag tctacccgct     300 cttgcgaaac aactatattg taaggaaaat atccagccag gtcaaattaa tatgcaaggg     360
gtttggtctt tcgccaagtc taataatgat tgatggtagg attccatcta aatc          414
```

<210> SEQ ID NO 20
<211> LENGTH: 1655
<212> TYPE: DNA
<213> ORGANISM: Arabidopsis thaliana

<400> SEQUENCE: 20

| | | | | | |
|---|---|---|---|---|---|
| atgactaata | ctctctgttt | aagcctcatc | accctaataa | cgcttttat | aagtttaacc | 60 |
| ccaaccttaa | tcaaatcaga | tgagggcatt | gatgttttct | tacccatatc | actcaacctt | 120 |
| acggtcctaa | ccgatccctt | ctccatctct | gccgcttctc | acgacttcgg | taacataacc | 180 |
| gacgaaaatc | ccggcgccgt | cctctgccct | tcctccacca | cggaggtggc | tcgtctcctc | 240 |
| cgtttcgcta | acggaggatt | ctcttacaat | aaaggctcaa | ccagcccgc | gtctactttc | 300 |
| aaagtggctg | ctcgaggcca | aggccactcc | ctccgtggcc | aagcctctgc | acccggaggt | 360 |
| gtcgtcgtga | acatgacgtg | tctcgccatg | gcggctaaac | cagcggcggt | tgttatctcg | 420 |
| gcagacggga | cttacgctga | cgtggctgcc | gggacgatgt | gggtggatgt | tctgaaggcg | 480 |
| gcggtggata | gaggcgtctc | gccggttaca | tggacggatt | atttgtatct | cagcgtcggc | 540 |
| gggacgttgt | cgaacgctgg | aatcggtggt | cagacgttta | gacacggccc | tcagattagt | 600 |
| aacgttcatg | agcttgacgt | tattaccgga | aaaggtgaaa | tgatgacttg | ctctccaaag | 660 |
| ttaaaccctg | aattgttcta | tggagtttta | ggaggtttgg | gtcaattcgg | tattataacg | 720 |
| agggccagga | ttgcgttgga | tcatgcaccc | acaagggtga | atggtctcg | catactctac | 780 |
| agtgacttct | cggcttttaa | aagagaccaa | gagcgtttaa | tatcaatgac | caatgatctc | 840 |
| ggagttgact | ttttggaagg | tcaacttatg | atgtcaaatg | gcttcgtaga | cacctctttc | 900 |
| ttcccactct | ccgatcaaac | aagagtcgca | ctcttgtga | atgaccaccg | gatcatctat | 960 |
| gttctcgaag | tagccaagta | ttatgacaga | accacccttc | ccattattga | ccaggtgatt | 1020 |
| gacacgttaa | gtagaactct | aggtttcgct | ccagggttta | tgttcgtaca | agatgttccg | 1080 |
| tatttcgatt | tcttgaaccg | tgtccgaaac | gaagaagata | aactcagatc | tttaggacta | 1140 |
| tgggaagttc | ctcatccatg | gcttaacatc | tttgtcccgg | ggtctcgaat | ccaagatttt | 1200 |
| catgatggtg | ttattaatgg | ccttcttcta | aaccaaacct | caacttctgg | tgttactctc | 1260 |
| ttctatccca | caaaccgaaa | caaatggaac | aaccgcatgt | caacgatgac | accggacgaa | 1320 |
| gatgtttttt | atgtgatcgg | attactgcaa | tcagctggtg | gatctcaaaa | ttggcaagaa | 1380 |
| cttgaaaatc | tcaacgacaa | ggttattcag | ttttgtgaaa | actcgggaat | taagattaag | 1440 |
| gaatatttga | tgcactatac | aagaaaagaa | gattgggtta | acattttgg | accaaaatgg | 1500 |
| gatgattttt | taagaaagaa | aattatgttt | gatcccaaaa | gactattgtc | tccaggacaa | 1560 |
| gacatatttta | attaacttat | cacatgtctt | aattaatttg | ttatgtaact | ttagaacgta | 1620 |
| tttttataac | atatacagac | aagtacgttc | atcgt | | | 1655 |

<210> SEQ ID NO 21
<211> LENGTH: 1873
<212> TYPE: DNA
<213> ORGANISM: Arabidopsis thaliana

<400> SEQUENCE: 21

| | | | | | |
|---|---|---|---|---|---|
| acagacaaac | aaaaaaaggt | ttggttccaa | aagctaaaaa | gcttccatct | acattagagt | 60 |
| ctctctattt | agcatttaca | cacaatcaca | cacacacaca | cacacacaca | ccaaaatgat | 120 |
| agcttacata | gaaccatact | tcttggaaaa | cgacgccgag | gctgcctctg | ccgccaccgc | 180 |
| cgccggaaaa | tctacggatg | gtgtttctga | gtcacttaac | atccaaggag | aaatcttatg | 240 |

-continued

| | |
|---|---|
| tggtggagct gcggcggata tcgccgggag agattttggc ggcatgaact gtgtgaagcc | 300 |
| tcttgctgtg gtgagaccag tgggaccgga agatatcgcc ggagcggtga aagcggctct | 360 |
| gaggtcagat aaactaacgg tggcggcgcg tggaaacggc cattctatca acggtcaagc | 420 |
| catgcggaa ggaggactcg ttgtcgatat gagtaccacg gcggagaatc atttcgaggt | 480 |
| tggttattta tccggcggtg atgccacggc gtttgttgat gtctccggag gggcattatg | 540 |
| ggaagatgta ttgaaacggt gcgtttcgga gtacggtttg gctccgaggt cttggactga | 600 |
| ttatcttggg ttaacggtgg gaggtacgtt gtcaaatgcc ggcgttagtg gtcaagcgtt | 660 |
| ccgttacgga ccacagacgt caaatgtaac ggagttggac gtcgttacgg gaaatggtga | 720 |
| cgtcgttact tgctcggaga ttgagaattc agagctattc ttctctgttt taggtggtct | 780 |
| tggtcagttt ggtatcatca ccagagctag gttttgcta cagccagctc ctgatatggt | 840 |
| gagatggata agagtagtat acaccgagtt cgatgagttc actcaagacg ccgagtggct | 900 |
| agtaagtcag aagaacgagt catcgttcga ttacgtggaa ggattcgtgt tgtcaacgg | 960 |
| tgctgacccg gttaacggat ggccaacagt tcccctccac ccggaccacg agtttgaccc | 1020 |
| gacccgacta ccacaatctt gcgggtcggt tctttattgc ctcgaactcg gtcttcacta | 1080 |
| cagagactcc gattccaact caaccattga caagagggtg gagagattga tcggacggct | 1140 |
| aagatttaat gaaggattaa gattcgaggt agatctgccg tacgttgact tttactacg | 1200 |
| agtcaaacgg tcagaagaaa tcgcgaagga gaacggtacg tgggaaacgc ctcacccttg | 1260 |
| gctcaacctc ttcgtgtcga agcgagacat cggagatttc aatcggacgg tgttcaaaga | 1320 |
| acttgtcaag aacggagtca atggtccaat gcttgtgtac ccactcttgc gaagcaggtg | 1380 |
| ggatgatcgg acgtccgtgg ttataccgga agaaggagag atattctaca ttgtggcatt | 1440 |
| gcttcggttc gtgccgccgt gtgcgaaagt ctcttcggta gagaaaatgg tagctcaaaa | 1500 |
| ccaagagatc gttcattggt gtgtcaaaaa cggaattgat tacaaattgt atcttcctca | 1560 |
| ttacaagtct caagaggaat ggattcgcca ttttggaaac cgatggtcga gatttgttga | 1620 |
| taggaaagct atgtttgatc ccatggctat actttcaccg ggtcaaaaga ttttcaatag | 1680 |
| gtctctttga cccctcatat ttttactttt tttacttttc ttatttttac ttttgtattc | 1740 |
| ttgagttttg tggtctttat gtaatttttt ctgtatttt cttttttccc aagaaaaaaa | 1800 |
| tcagctggtt ttttataaaa ggtggcctac gagtcatgtc caattatgaa taacaagaaa | 1860 |
| aaaaaaaaaa aaa | 1873 |

<210> SEQ ID NO 22
<211> LENGTH: 1857
<212> TYPE: DNA
<213> ORGANISM: Hordeum vulgare

<400> SEQUENCE: 22

| | |
|---|---|
| tgcagtgaac cactaccctg ctacacgcct ttcatctttc tcctgaaaac ctcaccacta | 60 |
| aacttattta ttcttgacct acagaagagc catgaggcaa ttactcctgc aatacctgaa | 120 |
| gctgttcctg ttgctaggcc ttggcgcagt cactgctgag catgtgctta acatgatgt | 180 |
| gcttgcatcc ctggggacgc tccccttga cgggcatttc agcttccacg acttgtctgc | 240 |
| agctgcaatg gacttcggca acctctctag cttcccgcca gtcgctgtgc ttcacccagg | 300 |
| ttcagtggct gacattgcca caaccgtgag gcatgtgttc ttgatgggtg agcactccgc | 360 |
| gctcacagtg gcagctcgtg ggcatggaca ctcgctatat gggcagtccc aggctgctgg | 420 |
| agggattgtc atcagaatgg aatcccttcg gagtgtcaaa atgcaggtgc atcctggtgc | 480 |

```
atcaccctat gtggatgcct caggaggcga actctggata aatgtcttga ataagacgtt    540
gaagtatggt ttggcgccga agtcatggac agactacctc caccttacgg ttgggggcac    600
gttgtcaaat gcgggcgtca gcgggcagac attccggcat ggtccacaga tcagcaatgt    660
gaacgaattg gagattgtga ctggaagagg tgatattgtc acttgctcac cagaacagaa    720
ctctgatctc ttccgtgctg ctcttggtgg tctgggtcag tttggcatca ttactcgggc    780
caggatcgca cttgagcctg ctccacaaat ggtgaggtgg ataagagttc tctacttaga    840
tttcatgagc ttcaccgagg atcaggagat gcttatttca gcagagaaga ccttcgacta    900
cattgaaggt ttcgttatca taaacagaac aggcatccta acaactgga ggtcatcgtt    960 caatccacag gacccagagc gggctagccg gttcgaaaca gacagaaaag tgctcttctg   1020
cctcgagatg acaaagaact tcaaccctga agaagctgac atcatggaac aggaggtcca   1080
tgcactacta tctcaactta gatacacacc agcctcctta ttccacacgg acgtcactta   1140
cattgagttc ttggataggg tgcactcctc tgagatgaag ctgagagcta agggcttgtg   1200
ggaagtccca cacccatggc ttaatctcat cataccaaga agcactatcc atacatttgc   1260
agagcaggtc tttgggaaaa tcctcgaaga taacaacaat ggtcccatat tgctctaccc   1320
agtgaagaag tccagatggg acaaccgaac gtcagtggtc ataccagatg aggaagtttt   1380
ctacctggtg ggattcctat cctcggcgat aggcccccac agcatcgaac atacattgaa   1440
cctgaacaac cagataatag agttctctaa caaagcaagt attggggtga agcaatatct   1500
tccaaactac accacagaac ccgagtggaa ggcccactat ggggctaggt gggacgcatt   1560
tcaacagagg aaaaacacct atgacccccct ggcaatccta gctccaggac agaaaatatt   1620
tcaaagaaaa ccagcatcac tacccttgtc ctcgttacag tacctactgt aaaaaatata   1680
tatgtggagc aatatgtcta tgttagtatg gaactatagt cgctttgcaa aagataacga   1740
actgcagcgt gaaggacact gtacagagta gtgactatta gtagtggtga tgctcaaaat   1800
acttttagca ctgagatcaa tgaagatcag caatgacata aaaaaaaaaa aaaaaaa     1857

<210> SEQ ID NO 23
<211> LENGTH: 413
<212> TYPE: DNA
<213> ORGANISM: Hordeum vulgare

<400> SEQUENCE: 23
cctcatccct ggctcaacgt gctcgtgccc cgctccggca tcgccgactt cgaccgcgcc     60
gtcttcaggg gcatcctcca gggcaccgac atcgccgggc cctcgtcgt ctacccactc    120 aacaaatcca gtgggacga cggcatgtcg gcggtgacgc cggcggagga ggtgttctac    180
gcggtgtcga tgctcttctc gtcggtggcc aacgacctga ggcggctgga ggcgcagaac    240
cagaagatac tgcggttctg cgacctcgcc gggatagggt acaaggagta cctggcgcac    300
tacacggccc acggcgactg ggtccggcac ttcgcggca agtggaagca cttcgtggag    360
atgaaggaca agtacgaccc caagaagctg ctctccccgg gccaagacat ctt          413

<210> SEQ ID NO 24
<211> LENGTH: 413
<212> TYPE: DNA
<213> ORGANISM: Triticum aestivum

<400> SEQUENCE: 24
cctcatccgt ggttgaacgt gctcgtgccc cgctcccgca tcgccgactt cgacagcgcc     60
gtcttcaagg gcatcctcca gggcaccgac atcgccgggc ccctcgtcgt ctacccactc    120
```

-continued

```
aacaaatcca agtgggacga cggcatgtcg gcggtgacgc cggcggagga ggtgttctac      180
gcggtgtcgc tgctcttctc gtcggtggcc aacgacctga agcggctgga ggcgcagaac      240
cagaagatac tgcggttctg cgacctcgcc gggatagggt acaaggagta cctggcgcac      300
tacacggccc acggcgactg ggtccggcac ttcggcggca agtggcagcg cttcgtggag      360
atgaaggaca agtacgaccc caagaggctg ctctccccag gccaggacat ctt             413
```